United States Patent

Elder et al.

(10) Patent No.: US 6,900,345 B2
(45) Date of Patent: May 31, 2005

(54) PLEUROMUTILIN DERIVATIVES

(75) Inventors: John Stephen Elder, Harlow (GB); Andrew Keith Forrest, Harlow (GB); Richard Lewis Jarvest, Harlow (GB); Robert John Sheppard, Harlow (GB)

(73) Assignee: SmithKline Beecham p.l.c., Brentford (GB)

(*) Notice: Subject to any disclaimer, the term of this patent is extended or adjusted under 35 U.S.C. 154(b) by 0 days.

(21) Appl. No.: 10/399,023

(22) PCT Filed: Oct. 8, 2001

(86) PCT No.: PCT/EP01/11603

§ 371 (c)(1),
(2), (4) Date: Jul. 25, 2003

(87) PCT Pub. No.: WO02/30929

PCT Pub. Date: Apr. 18, 2002

(65) Prior Publication Data

US 2004/0024059 A1 Feb. 5, 2004

(30) Foreign Application Priority Data

Oct. 10, 2000 (GB) .............................................. 0024811

(51) Int. Cl.$^7$ .............................................. C07C 26/00
(52) U.S. Cl. ........................ 560/115; 560/158; 514/547
(58) Field of Search ................................ 560/115, 158; 514/547

(56) References Cited

FOREIGN PATENT DOCUMENTS

| WO | WO 97/25309 | 7/1997 |
|----|-------------|--------|
| WO | WO 98/05659 | 2/1998 |
| WO | WO 99/21855 | 5/1999 |
| WO | WO 01/14310 | 3/2001 |
| WO | WO 01/74788 | 10/2001 |

*Primary Examiner*—Paul J. Killos
(74) *Attorney, Agent, or Firm*—James C. Kellerman; Stephen Venetianer; Charles M. Kinzig

(57) ABSTRACT

Pleuromutilin compounds of the formula:

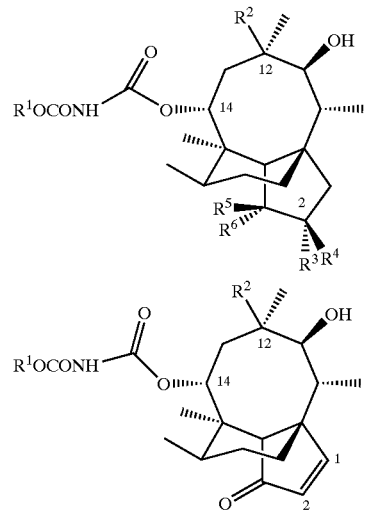

are of use in anti-bacterial therapy.

13 Claims, No Drawings

PLEUROMUTILIN DERIVATIVES

The present invention relates to novel compounds, to processes for their preparation, to pharmaceutical compositions containing them and to their use in medical therapy, particularly antibacterial therapy.

Pleuromutilin, the compound of formula (A), is a naturally occurring antibiotic which has antimycoplasmal activity and modest antibacterial activity. Mutilin and other compounds with a free OH at C-14 are inactive. The impact of further modification at C-14 on the activity of pleuromutilin has been investigated (H. Egger and H. Reinshagen, J. Antibiotics, 1976, 29, 923). Replacing the hydroxy group of the glycolic ester moiety at position 14 by another O, S or N-linked group was found to improve anti-microbial activity. Thus, introducing a diethylaminoethylthio group gives the compound of formula (B), also known as Tiamulin, which is used as a veterinary antibiotic (G. Hogenauer in, Antibiotics, Vol. V, part 1, ed. F. E. Hahn, Springer-Verlag, 1979, p.344).

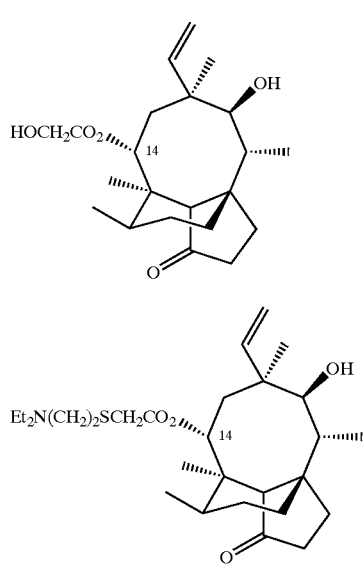

In this application, the non-conventional numbering system which is generally used in the literature (G. Hogenauer, loc. cit.) is used.

WO 97/25309 (SmithKline Beecham) describes further modification of the acyloxy group, disclosing inter alia 14-O-carbamoyl ($R^aONR^bCO_2$— and $R^aCONR^bCO_2$—) derivatives of mutilin in which $R^a$ may have a range of values, including saturated or unsaturated optionally substituted (cyclic) hydrocarbon, or an optionally substituted aryl or heterocyclic group and $R^b$ is a selected from a variety of monovalent groups.

WO 98/05659 (SmithKline Beecham) describes further 14-O-carbamoyl derivatives of mutilin in which the N-atom of the carbamoyl group is acylated by a group which includes an azabicyclic moiety.

WO 99/21855 (SmithKline Beecham) describes further derivatives of mutilin or 19,20-dihydromutilin, in which the glycolic ester moiety at position 14 is replaced by the group $R^2(CH_2)_mX(CH_2)_nCH_2COO$— in which $R^2$ is a non-aromatic mono- or bicyclic group.

WO 00/27790 (SmithKline Beecham) describes C-14 spirocyclic, acylcarbamate, heteroarylalkyl carboxylate or arylalkoxyalkyl carboxylate derivatives of mutilin or 19,20-dihydromutilin.

WO 00/37074 (SmithKline Beecham) describes further derivatives of mutilin or 19,20-dihydromutilin having a heteroaryl acetate substituent at the C-14 position.

WO 00/3287 (SmithKline Beecham) describes further derivatives of mutilin or 19,20-dihydromutilin having an isoxazoline carboxylate substituent at the C-14 position.

WO 01/14310 (SmithKline Beecham) describes further derivatives of mutilin or 19,20-dihydromutilin having a β-ketoester substituent at the C-14 position.

In addition, 19,20-dihydro-2a-hydroxy-mutilin is described by G. Schulz and H. Berner in Tetrahedron, 1984, vol. 40, pp 905–917, and a number of C-14 ether, carbamate, amide and urea derivatives of mutilin or 19,20-dihydromutilin are described by Brooks et al. in Bioorg. Med. Chem, 2001, vol. 9, pp1221–1231.

The present invention is based on the unexpected discovery that certain novel C-14 oxycarbonyl carbamate derivatives of mutilin have potent antimicrobial activity.

Accordingly the present invention provides a compound of formula (IA) or (IB):

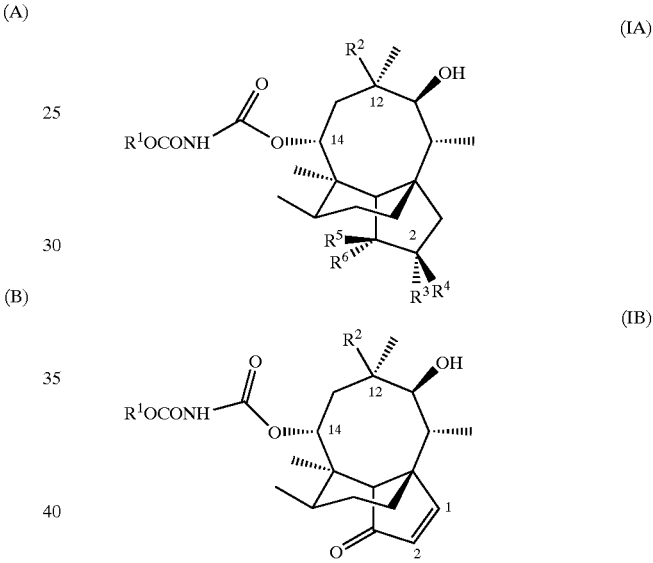

in which:
$R^1$ is optionally substituted $C_{(1-6)}$alkyl or $C_{(3-6)}$cycloalkyl or optionally substituted heterocyclyl;
$R^2$ is vinyl or ethyl;
$R^3$ is H, OH or F, and $R^4$ is H, or $R^3$ is H and $R^4$ is F, and $R^5$ and $R^6$ together form an oxo group; or
$R^3$ and $R^4$ is each H, $R^5$ is OH or H and $R^6$ is H, or $R^5$ is H and $R^6$ is OH or H.

Examples of compounds of formula (IA) include those in which $R^3$ and $R^4$ are both hydrogen, and $R^5$ and $R^6$ together form an oxo group.

Further examples of compounds of formula (IA) include those in which $R^3$ is OH and $R^4$ is hydrogen, and $R^5$ and $R^6$ together form an oxo group.

Representative substituents for $R^1$ include 1, 2 or 3 substituents selected from hydroxy, $C_{(1-6)}$alkylsulfonyl, optionally substituted aryl, optionally substituted heteroaryl, optionally substituted heterocyclyl, carbamoyl, $C_{(1-6)}$alkylcarbonylamino, $C_{(1-6)}$alkylsulfonylamino, and ureido.

Preferred substituents for $R^1$ include hydroxy, fluoro, carbamoyl$C_{(1-6)}$alkyl, carbamoyloxy, carbamoyloxy$C_{(1-6)}$alkyl, cyano, cyano$C_{(1-6)}$alkyl, ureido (optionally substituted by $C_{(1-6)}$alkyl), guanidino, $C_{(1-6)}$alkylguanidino, amidino, $C_{(1-6)}$alkylamidino, oxamoyl, amino (optionally substituted by, for example, 1 or 2 substituents which may be the same or different selected from oxamoyl (optionally substituted on N by hydroxy($C_{1-6}$)alkyl), acyl, ($C_{1-6}$)alkylsulphonyl, ($C_{1-6}$) alkyl (optionally substituted by, for example, hydroxy), acyl, arylcarbonyl and carbamoyl($C_{1-6}$)alkyl), mono- and di-($C_{1-6}$)alkylamino($C_{1-6}$)alkyl, amino$C_{(1-6)}$alkyl, amino($C_{1-6}$) alkylcarbonyl, sulphonylamino, aminosulphonyl and $R^7R^8NCO$ wherein $R^7$ and $R^8$ which may be the same or different is each selected from hydrogen, ($C_{1-6}$)alkyl, ($C_{1-6}$) alkoxy, ($C_{1-6}$)alkoxy($C_{1-6}$)alkyl, cyano($C_{1-6}$)alkyl and heteroaryl($C_{1-6}$)alkyl or $R^7$ and $R^8$ together with the nitrogen atom to which they are attached form a heterocyclyl ring.

Representative examples of $R^1$ include:
(a) $C_{(1-6)}$alkyl optionally substituted by 1, 2 or 3 substituents selected from
heteroaryl optionally substituted by 1, 2 or 3 substituents selected from $C_{(1-6)}$alkyl, hydroxy$C_{(1-6)}$alkyl, amino, amino$C_{(1-6)}$alkyl, carbamoyl, cyano and hydroxy,
heterocyclyl optionally substituted by 1, 2 or 3 substituents selected from oxo, $C_{(1-6)}$alkyl, hydroxy$C_{(1-6)}$alkyl, aminosulphonyl, carbamoyl and acyl,
amino substituted by 1 or 2 substituents which may be the same or different selected from oxamoyl (optionally substituted on N by hydroxy($C_{1-6}$)alkyl), acyl, ($C_{1-6}$) alkylsulphonyl, ($C_{1-6}$)alkyl (optionally substituted by, for example, hydroxy), and carbamoyl($C_{1-6}$)alkyl,
carbamoyloxy, ureido substituted by $C_{(1-6)}$alkyl, $C_{(1-6)}$ alkylsulphonyl, hydroxy, halogen, $C_{(1-6)}$alkylthio, and $R^7R^8NCO$ wherein $R^7$ and $R^8$ which may be the same or different is each selected from hydrogen, ($C_{1-6}$)alkyl, ($C_{1-6}$) alkoxy, ($C_{1-6}$)alkoxy($C_{1-6}$)alkyl, cyano($C_{1-6}$)alkyl and heteroaryl($C_{1-6}$)alkyl or $R^7$ and $R^8$ together with the nitrogen atom to which they are attached form a heterocyclyl ring,
(b) $C_{(3-6)}$cycloalkyl substituted by amino, carbamoyl or di-$C_{(1-6)}$alkylamino$C_{(1-6)}$alkyl, and
(c) a 4- to 6-membered heterocyclyl ring or two fused 5-membered heterocyclyl rings containing 1 or 2 heteroatoms in each ring (for example tetrahydrofuran, 1,3-dioxane, hexahydrofuro[3,2-b]furan, trimethylenesulphide, tetrahydrothiophene, azetidine, pyrrolidine, isoxazolidine or piperidine) optionally substituted by 1, 2 or 3 substituents selected from $C_{(1-6)}$alkyl, hydroxy, hydroxy$C_{(1-6)}$alkyl, $C_{(1-6)}$alkylsulphonyl, $C_{(1-6)}$ alkoxy, oxo, oxamoyl, carbamoyl, carbamoyl$C_{(1-6)}$alkyl, carbamoyloxy, carbamoyloxy$C_{(1-6)}$alkyl, amino$C_{(1-6)}$ alkylcarbonyl, amino (optionally substituted by oxamoyl), $C_{(1-6)}$alkoxyimino, azido, cyano, cyano($C_{1-6}$) alkyl, and heteroarylcarbonyl (optionally substituted by, for example, amino).

Typical examples of $R^1$ include, for example, methyl, hydroxyethyl, and methylsulfonylethyl.

Preferred examples of $R^1$ include $C_{(1-6)}$alkyl substituted by carbamoyloxy, $C_{(1-6)}$alkyl substituted by hydroxy and di-N—$C_{(1-6)}$alkylamino, $C_{(3-6)}$cycloalkyl substituted by di-$C_{(1-6)}$alklamino$C_{(1-6)}$alkyl and a 4- or 5-membered heterocyclyl ring containing one nitrogen atom optionally substituted by oxo.

Representative examples of groups for $R^3$ include H and OH.

Representative examples of groups for $R^4$ include H.
Preferably, $R^3$ and $R^4$ is each H.
Preferably, $R^5$ and $R^6$ together form an oxo group.
When used herein, the term "aryl" refers to, unless otherwise defined, phenyl or naphthyl. A substituted aryl group comprises up to five, preferably up to three substituents.

Suitable substituents for an aryl group, including phenyl when forming part of a benzyl group, include, for example, and unless otherwise defined, halogen, ($C_{1-6}$)alkyl, aryl, aryl($C_{1-6}$)alkyl, ($C_{1-6}$)alkoxy, ($C_{1-6}$)alkoxy($C_{1-6}$)alkyl, halo ($C_{1-6}$)alkyl, aryl($C_{1-6}$)alkoxy, hydroxy, nitro, cyano, azido, amino, mono- and di-N-($C_{1-6}$)alkylamino, acylamino, arylcarbonylamino, acyloxy, carboxy, carboxy salts, carboxy esters, carbamoyl, mono- and di-N-($C_{1-6}$) alkylcarbamoyl, ($C_{1-6}$)alkoxycarbonyl, aryloxycarbonyl, ureido, guanidino, ($C_{1-6}$)alkylguanidino, amidino, ($C_{1-6}$) alkylamidino, sulphonylamino, aminosulphonyl, ($C_{1-6}$) alkylthio, ($C_{1-16}$)alkylsulphinyl, ($C_{1-16}$)alkylsulphonyl, heterocyclyl, heteroaryl, heterocyclyl($C_{1-6}$)alkyl and heteroaryl($C_{1-6}$)alkyl. In addition, two adjacent ring carbon atoms may be linked by a ($C_{3-5}$)alkylene chain, to form a carbocyclic ring.

Further suitable substituents for an aryl group include substituted ($C_{1-6}$)alkyl, substituted amino, amino($C_{1-6}$)alkyl, amino($C_{1-6}$)alkylcarbonyl, oxamoyl, carbamoyl($C_{1-6}$)alkyl, cyano($C_{1-6}$)alkyl, acyl, carbamoyloxy, carbamoyloxy($C_{1-6}$) alkyl and optionally substituted heteroarylcarbonyl.

When used herein, the terms "alkyl" and "alkenyl" refer to (individually or as part of alkoxy or alkenyloxy) straight and branched groups containing up to six carbon atoms.

When used herein, the terms "cycloalkyl" and "cycloalkenyl" refer to groups having from three to eight ring carbon atoms.

When substituted, an alkyl, alkenyl, cycloalkyl or cycloalkenyl group may comprise up to four substituents, preferably up to two substituents.

Suitable substituents for alkyl, alkenyl, cycloalkyl or cycloalkenyl groups include aryl, heteroaryl, heterocyclyl, ($C_{1-6}$)alkoxy, ($C_{1-6}$)alkylthio, aryl($C_{1-6}$)alkoxy, aryl($C_{1-6}$) alkylthio, amino, mono- or di-($C_{1-6}$)alkylamino, cycloalkyl, cycloalkenyl, carboxy and esters thereof, carbamoyl, ureido, guanidino, ($C_{1-6}$)alkylguanidino, amidino, ($C_{1-6}$) alkylamidino, ($C_{1-6}$)acyloxy, azido, hydroxy, and halogen.

Further suitable substituents for alkyl, alkenyl, cycloalkyl or cycloalkenyl groups include substituted aryl, substituted heteroaryl, substituted heterocyclyl, substituted amino, carbamoyloxy, ureido substituted by ($C_{1-6}$)alkyl, ($C_{1-6}$) alkylsulphonyl, mono- or di-($C_{1-6}$)alkylamino($C_{1-6}$)alkyl, and carbamoyl substituted by 1 or 2 substituents which may be the same or different selected from ($C_{1-6}$)alkyl, ($C_{1-6}$) alkoxy, ($C_{1-6}$)alkoxy($C_{1-6}$)alkyl, cyano($C_{1-6}$)alkyl and heteroaryl($C_{1-6}$)alkyl, or carbamoyl substituted by 2 substituents which together with the nitrogen atom to which they are attached form a heterocyclyl ring.

Preferred substituents for cycloalkyl include hydroxy, amino, carbamoyl and di-$C_{(1-6)}$alkylamino$C_{(1-6)}$alkyl.

When used herein the terms "heterocyclyl" and "heterocyclic" refer to, unless otherwise defined, non-aromatic, single, bridged and fused, rings suitably containing up to four heteroatoms in each ring, each of which is selected from oxygen, nitrogen and sulphur. Each heterocyclic ring preferably has from 4 to 7, preferably 5 or 6, ring atoms. A fused heterocyclic ring system may include carbocyclic rings and need include only one heterocyclic ring.

Representative examples of heterocyclyl rings include non-aromatic, saturated rings containing 1 or 2 heteroatoms and having 4 to 7, in particular 5 or 6, atoms in each ring, for example tetrahydrofuran, 1,3-dioxolane, 1,3-dioxane, hexahydrofuro[3,2-b]furan, trimethylenesulphide, tetrahydrothiophene, azetidine, pyrrolidine, oxazolidine, isoxazolidine, piperidine, piperazine, morpholine and thiomorpholine. Preferably the heterocyclyl ring contains 1 or 2 nitrogen atoms.

When substituted, a heterocyclyl group may comprise up to three substituents. Preferably a substituent for a heterocyclyl group is selected from oxo, $C_{(1-6)}$alkylimino, and the groups hereinbefore defined as suitable aryl substituents.

Representative examples of non-aromatic, unsaturated heterocyclyl rings subsituted by oxo include, for example, pyridone and optionally substituted uracil.

When used herein, the term "heteroaryl" suitably includes, unless otherwise defined, a mono- or bicyclic heteroaromatic ring system comprising up to four, preferably 1 or 2, heteroatoms each selected from oxygen, nitrogen and sulphur. Each ring may have from 4 to 7, preferably 5 or 6, ring atoms. A bicyclic heteroaromatic ring system may include a carbocyclic ring.

Representative examples of heteroaryl rings includes pyrazole, isoxazole, pyridine, pyrimidine and pyrazine.

When substituted, a heteroaryl group may comprise up to three substituents. Preferably a substituent for a heteroaryl group is selected from the group hereinbefore defined as suitable aryl substituents.

When used herein, the term "acyl" includes formyl and $(C_{1-6})$alkylcarbonyl.

When used herein, the term "sulfonyl" includes $(C_{1-6})$alkylsulfonyl.

The term halo or halogen includes fluoro, chloro, bromo and iodo.

When used herein, the term "substituted amino", unless otherwise defined, refers to an amino group substituted by 1 or 2 substituents.

Suitable substituents for an amino group include oxamoyl (optionally substituted on N by hydroxy$(C_{1-6})$alkyl), acyl, $(C_{1-6})$alkylsulphonyl, $(C_{1-6})$alkyl (optionally substituted by, for example, hydroxy), and carbamoyl$(C_{1-6})$alkyl.

It will be appreciated that depending on the substituents at the C-14 position certain compounds of the present invention may comprise one or more chiral centres so that compounds may exist as stereoisomers, including diastereomers and epimers. The present invention covers all such stereoisomers, and mixtures thereof, including racemates.

Depending on the substituents, two or more diastereoisomers may be possible. In that situation the present invention includes the individual diastereoisomers and mixtures thereof The 2-hydroxy-substituted compounds of formula (I) are of the 2 (S) configuration.

Preferred compounds of the invention include:
Mutilin 14-[N-(2-carbamoyloxyethoxycarbonyl)] carbamate;
Mutilin 14-[N-(2-oxopyrrolidin-3-(S)-yloxycarbonyl)] carbamate;
Mutilin 14-[N-(azetidinyloxycarbonyl)]carbamate hydrochloride;
Mutilin 14-[N-(pyrrolidin-3-(R)-yloxycarbonyl)]carbamate;
Mutilin 14-[N-(pyrrolidin-3-(S)-yloxycarbonyl)]carbamate;
Mutilin 14-[N-(3-dimethylamino-2-hydroxyprop-1-yloxycarbonyl)]carbamate; and
Mutilin 14-[N-(1-(dimethylaminomethyl) cyclopropoxycarbonyl)]carbamate.

Particularly preferred compounds of the invention include:
Mutilin 14-[-(pyrrolidin-3-(R)-yloxycarbonyl)]carbamate; and
Mutilin 14-[N-(pyrrolidin-3-(S)-yloxycarbonyl)]carbamate.

The compounds of this invention may be in crystalline or non-crystalline form, and, if crystalline, may optionally be hydrated or solvated. This invention includes within its scope stoichiometric hydrates as well as compounds containing variable amounts of water.

The compounds according to the invention are suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight.

Compounds of the invention that contain a basic group such as an amino substituent may be in the form of a free base or an acid addition salt. Compounds having an acidic group such as a carboxy substituent may be in the form of a pharmaceutically acceptable salt. Compounds of the invention having both a basic and an acidic centre may be in the form of zwitterions, acid addition salt of the basic centre or alkali metal salts (of the carboxy group). Pharmaceutically acceptable salts are preferred.

Pharmaceutically acceptable acid-addition salts include those described by Berge, Bighley, and Monkhouse, *J. Pharm. Sci.*, 1977, 66, 1–19. Suitable salts include the hydrochloride, maleate, and methanesulfonate; particularly the hydrochloride.

Pharmaceutically acceptable salts for acidic groups include those described by Berge, Bighley, and Monkhouse, *J. Pharm. Sci.*, 1977, 66, 1–19. Suitable salts include alkali metal salts such as the sodium and potassium salts.

Compounds of the present invention may be readily prepared from a (epi-) mutilin or a 19,20-dihydro-mutilin compound by adapting procedures well known in the art for forming carbamate groups. Representative processes are described in WO 97/25309 and WO 98/05659 (SmithKline Beecham plc). In a preferred process, a chloroformate derivative is reacted with silver cyanate followed by reaction with an alcohol. It will be appreciated that the (epi-) mutilin or a 19,20-dihydro-mutilin compound may provide either the alcohol or the chloroformate component.

Accordingly, the present invention provides a process for preparing a compound of formula (IA) or (IB) which process comprises reacting a chloroformate compound of formula (IIA) or (IIB):

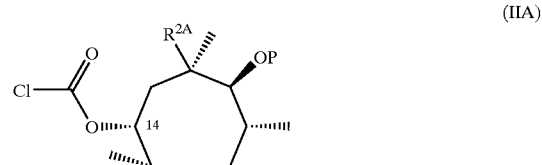

(IIA)

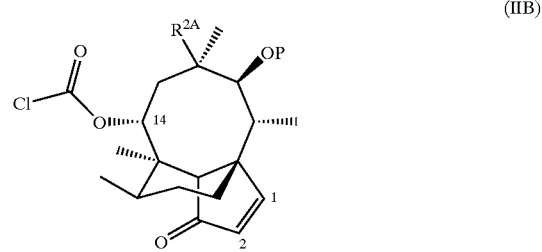

(IIB)

in which:
P is hydrogen or an hydroxy-protecting group;
$R^{2A}$, $R^{3A}$, $R^{4A}$, $R^{5A}$ and $R^{6A}$ are $R^2$, $R^3$, $R^4$, $R^5$ and $R^6$ as defined for formulae (IA) and (IB) or a group convertible to $R^2$, $R^3$, $R^4$, $R^5$ and $R^6$ respectively;
with silver cyanate, in a suitable aprotic solvent, for instance dichloromethane, followed by treating with an alcohol compound of formula (III):

R¹ᴬOH   (III)

in which R¹ᴬ is R¹ as defined for formulae (IA) and (IB) or a group convertible to R¹;
in the presence of pyridine, in a carbamate forming reaction, and thereafter, and if so needed;
converting P to hydrogen, and, if necessary, converting an R²ᴬ, R³ᴬ, R⁴ᴬ, R⁵ᴬ and R⁶ᴬ group to an R², R³, R⁴, R⁵ and R⁶ group.

It will be appreciated that the process may be reversed so that a chloroformate derivative of the alcohol of formula (III) is reacted with silver cyanate, followed by addition of a pleuromutilin derivative of formula (IVA) or (IVB):

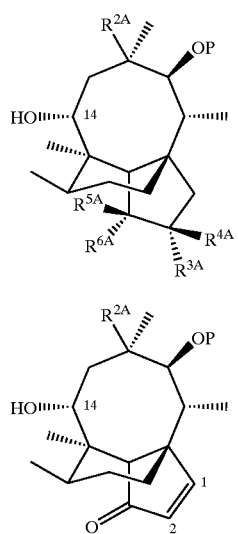

in which P, R²ᴬ, R³ᴬ, R⁴ᴬ, R⁵ᴬ and R⁶ᴬ are as hereinbefore defined.

Preparation of the chloroformate compounds of formula (IIA) and (IIB) are described in WO 97/25309 and WO 98/05659 (SmithKline Beecham plc).

Conversion of an R¹ᴬ, R²ᴬ, R³ᴬ, R⁴ᴬ, R⁵ᴬ or R⁶ᴬ group to an R¹, R², R³, R⁴, R⁵ and R⁶ group typically arises if a protecting group is needed during the above reactions or during the preparation of the reactants by the procedures described below.

When P is a hydroxyl protecting group, a preferred protecting group is acyl, for example so that —OP is trifluoroacetoxy or dichloroacetoxy. When the intended R³, R⁵ or R⁶ is also hydroxyl, then R³ᴬ, R⁵ᴬ and R⁶ᴬ is also preferably acyloxy, for example acetoxy or dichloroacetoxy. Hydroxyl groups at positions 11, 3 and 2 (as groups OP, R⁵ᴬ and R⁶ᴬ and R³ᴬ) may be protected using, for example, trifluoroacetic anhydride or dichloroacetic anhydride and pyridine in tetrahydrofuran or N-trifluoroacetyl-imidazole in tetrahydrofuran at 0° C. After the reaction described above with (III) is complete, the protecting acyl groups may be removed to restore the hydroxyl groups, for instance by hydrolysis e.g. using NaOH in either MeOH or tetrahydrofuran/water solution, or sodium hydrogen carbonate in aqueous ethanol.

Suitable hydroxy, carboxy and amino protecting groups are those well known in the art and which may be removed under conventional conditions and without disrupting the remainder of the molecule. A comprehensive discussion of the ways in which hydroxy, carboxy and amino groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991). Particularly suitable hydroxy protecting groups include, for example, triorganosilyl groups such as, for instance, trialkylsilyl and also organocarbonyl and organooxycarbonyl groups such as, for instance, acetyl, allyloxycarbonyl and 4-methoxybenzyloxycarbonyl. Particularly suitable carboxy protecting groups include alkyl and aryl esters, for instance methyl, ethyl and phenyl. Particularly suitable amino protecting groups include alkoxycarbonyl groups such as tert-butoxycarbonyl and benzyloxycarbonyl.

R²ᴬ is typically the R² group vinyl, and this may be converted to the alternative R² ethyl group by hydrogenating the vinyl group to form an ethyl group, typically by hydrogenation over a palladium catalyst (e.g. 10% palladium-on-carbon) in a solvent such as ethyl acetate, ethanol, dioxane, or tetrahydrofuran.

R³ᴬ is typically hydrogen, fluoro or protected hydroxyl, such as acyloxy. After the coupling reaction, if required, protecting acyl groups may be removed to restore the hydroxyl groups by hydrolysis e.g. using NaOH in MeOH, or sodium hydrogen carbonate in aqueous ethanol.

A compound of formula (IA) in which R³ and R⁴ are both hydrogen and R⁵ and R⁶ form an oxo group may also be prepared from an epi-mutilin starting material. Accordingly, in a further aspect, the present invention provides a process for preparing a compound of formula (IA) in which R³ and R⁴ are both hydrogen and R⁵ and R⁶ form an oxo group, which comprises reacting a chloroformate epi-mutilin compound of formula (IIC):

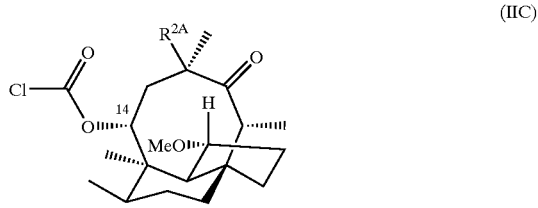

wherein R²ᴬ is as hereinbefore defined;
with silver cyanate and then a compound of formula (III), as hereinbefore defined; under carbamate forming conditions as hereinbefore described;
and then treating the product with an acid;
and where required or desired converting an R¹ᴬ group to an R¹ group and an R²ᴬ group to an R² group.

Alternatively, a chloroformate derivative of the alcohol of formula (III) may be treated initially with silver cyanate, followed by treatment with an epi-mutilin compound of formula (IID):

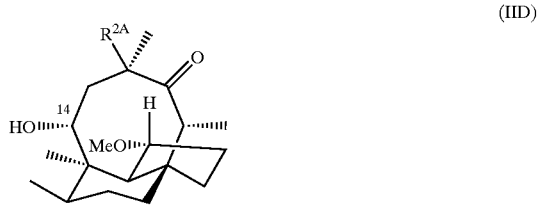

under carbamate forming conditions; and then
treating the product with an acid,
and where required or desired converting an R¹ᴬ group to an R¹ group and an R²ᴬ group to an R² group.

The acid treatment indicated above converts the epi-mutilin configuration to the usual mutilin nucleus of formula (IA). Typically this conversion is carried out by treatment with conc. HCl or Lukas reagent (conc. HCl saturated with $ZnCl_2$) in dioxane.

It should be appreciated that it may be necessary to interconvert one $R^1$, $R^2$, $R^3$, $R^4$, $R^5$ or $R^6$ group to another $R^1$, $R^2$, $R^3$, $R^4$, $R^5$ or $R^6$ group. This typically arises when one compound of formula (IA/B) is used as the immediate precursor of another compound of formula (IA/B) or when it is easier to introduce a more complex or reactive substituent at the end of a synthetic sequence. A substituent group in $R^1$ can be converted into another substituent group using one of the general methods for functional group transformation described in the literature (e.g. a carboxylic ester can be hydrolysed to a carboxylic acid with base; an acid can be converted into an amide; a tert-butoxycarbonylamino group can be converted into an amine by treatment with trifluoroacetic acid; an amino group can be alkylated or acylated), provided that the method chosen is compatible with other functional groups in the molecule (e.g. the ketone at C-3 in the pleuromutilin nucleus).

Functional group transformations are well known in the art and are described in, for instance, *Comprehensive Organic Functional Group Transformations*, eds. A. R. Katritzky, O. Meth-Cohn, and C. W. Rees (Elsevier Science Ltd., Oxford, 1995), *Comprehensive Organic Chemistry*, eds. D. Barton and W. D. Ollis (Pergamon Press, Oxford, 1979), and *Comprehensive Organic Transformations*, R. C. Larock (VCH Publishers Inc., New York, 1989).

Compounds of formulae (IIA) in which $R^{3A}$ and $R^{4A}$ are hydrogen, (IIB) and (IIC) may be readily prepared according to methods described in the literature, for example G. Schulz and H. Berner, *Tetrahedron*, 1984, 40, 905, and in WO 97/25309 and WO 98/05659 (SmithKline Beecham). Where necessary, and as hereinbefore described, saponification of the C-14 ester may be carried out at an appropriate stage.

Compounds of formula (IIA) in which $R^{3A}$ is hydroxyl or fluoro may be prepared from pleuromutilin, via an intermediate 2-diazo compound, the preparation of which is described by G. Schulz and H. Berner in *Tetrahedron*, 1984, 40, 905. Where necessary, saponification of the C-14 ester group may be carried out at an appropriate stage using conventional techniques such as sodium hydroxide or sodium methoxide in methanol or aqueous tetrahydrofuran solution.

The intermediate 2-diazo compound may be reacted with a carboxylic acid to give a 2-acyloxy-mutilin derivative. Suitably, reaction with dichloroacetic acid gives a 2-dichloroacetoxy-mutilin derivative, which can be deprotected as described above to provide the (2S)-2-hydroxy derivative, at an appropriate stage.

Compounds of formula (IIA) in which $R^{3A}$ is fluoro may be obtained by reacting 2-diazo-mutilin with a source of hydrogen fluoride. Conveniently, the hydrogen fluoride source is an amine complex of hydrogen fluoride such as hydrogen fluoride-pyridine. The reaction may be carried out in an anhydrous solvent (e.g. diethyl ether, tetrahydrofuran, 1,2-dimethoxyethane), at a temperature of −15° C. to 25° C. This reaction produces (2S)-2-fluoro derivatives. (2R)-2-Fluoro-mutilin derivatives may be prepared by treating the (2S)-isomer with a base (e.g. sodium hydroxide or potassium hydroxide in ethanol). This will usually produce a mixture of (2S) and (2R)-isomers that may be separated using conventional techniques such as chromatography and crystallisation.

Compounds of formula (IIA) in which $R^5$ is hydroxy and $R^6$ is hydrogen may be prepared according to methods described in the literature, for example, by reduction of a mutilin with lithium aluminium hydride as described by Birch et al, *Tetrahedron*, 1966, supp 8 (II), 359–387; or by reduction with lithium tri-tert-butoxyaluminohydride in dioxane as described by G. Schultz et al, *Tetrahedron*, 1984, 40, 905–917.

Compounds of formula (IIA) in which $R^5$ is hydrogen and $R^6$ is hydroxy may be prepared according to the methods described in the literature, for example, by reduction of a mutilin with lithium and methanol in liquid ammonia, as described by Birch et al, *Tetrahedron*, 1966, supp 8 (II), 359–387.

Compounds of formula (IIA) in which $R^5$ and $R^6$ are both hydrogen may be prepared according to the method of G. Schultz et al, *Tetrahedron*, 1984, 40, 905–917, by reduction with potassium hydroxide and hydrazine in refluxing diethylene glycol.

The compounds of the present invention may contain a chiral centre, and therefore the above processes may produce a mixture of diastereoisomers. A single diastereoisomer may be prepared by separating such a mixture of diastereoisomers by conventional techniques such as chromatography or fractional crystallisation.

The compounds of this invention may be in crystalline or non-crystalline form, and, if crystalline, may optionally be hydrated or solvated. When some of the compounds of this invention are allowed to crystallise or are recrystallised from organic solvents, solvent of crystallisation may be present in the crystalline product. Similarly, some of the compounds of this invention may be crystallised or recrystallised from solvents containing water. In such cases water of hydration may be present in the crystalline product. Crystallisation procedures will usually produce stoichiometric hydrates. Compounds containing variable amounts of water may be produced by processes such as lyophilisation.

The compounds according to the invention are suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

The present invention also includes pharmaceutically acceptable salts and derivatives of the compounds of the invention. Salt formation may be possible when one of the substituents carries an acidic or basic group. Salts may be prepared by salt exchange in conventional manner.

Acid-addition salts may be pharmaceutically acceptable or non-pharmaceutically acceptable. In the latter case, such salts may be useful for isolation and purification of the compound of the invention, or intermediates thereto, and will subsequently be converted into a pharmaceutically acceptable salt or the free base.

The compounds of the present invention and their pharmaceutically acceptable salts or derivatives have antimicrobial properties and are therefore of use in therapy, in particular for treating microbial infections in animals, especially mammals, including humans, in particular humans and domesticated animals (including farm animals). The compounds may be used for the treatment of infections caused by, for example, Gram-positive and Gram-negative bacteria and mycoplasmas, including, for example, *Staphylococcus aureus, Staphylococcus epidermidis, Enterococcus faecalis, Streptococcus pyogenes, Streptococcius agalactiae, Streptococcus pneumoniae, Haemophilus* sp.,

*Neisseria* sp., *Legionella* sp., *Chlamydia* sp., *Moraxella catarrhalis, Mycoplasma pneumoniae*, and *Mycoplasnia gallisepticum.*

In addition, compounds of this invention are active against bacterial organisms which are resistant (including multiply-resistant) to other anti-bacterial agents, for instance, β-lactam antibiotics such as, for example, methicillin; macrolides; and quinolones. Such bacterial organisms include, for example, methicillin resistant *Staphylococcius aureus* (MRSA) and drug-resistant *Streptococcus pneumoniae* (DRSP). Compounds of the present invention are therefore useful in the treatment of infections caused by these bacteria.

The present invention also provides a method of treating microbial infections in animals, especially in humans and in domesticated mammals, which comprises administering a compound of the invention or a pharmaceutically acceptable salt or derivative or solvate thereof, or a composition according to the invention, to a patient in need thereof.

Compounds of the present invention show good activity against *Chlamydia pneumoniae*. This has been implicated in heart disease, in particular in promoting vascular infection (see for instance FR 2,771,008-A1, Hoechst Marion Roussel S A). Accordingly, in a further aspect, the present invention provides a method of preventing *C pneumoniae*-induced atherosclerosis which method comprises treating a subject in need thereof with an effective amount of a compound of formula (I). A compound of formula (I) may also be used in combination with an anti-atherosclerotic agent, to reduce the incidence of heart attack and other cardiac events. Representative examples of anti-atherosclerotic agents include the class of cholesterol-lowering compounds referred to generically as "statins", for instance atorvastatin (Lipitor, Warner Lambert), pravastatin (Pravachol), simvastatin (Lipovas, Merck) and cerivastatin (Baycol, Bayer). It has also been suggested that *Chlamydia pneumoniae* may contribute to Alzheimer's Disease. Accordingly, in a further aspect, the present invention provides a method of treating Alzheimer's Disease which method comprises treating a subject in need thereof with an effective amount of a compound of formula (I).

The invention further provides the use of a compound of the invention or a pharmaceutically acceptable salt or derivative or solvate thereof in the preparation of a medicament for use in the treatment of microbial infections.

Compounds of the present invention may be used to treat skin and soft tissue infections and acne, by topical application. Accordingly, in a further aspect the present invention provides the use of a compound of the invention or a pharmaceutically acceptable salt or derivative or solvate thereof in the preparation of a medicament adapted for topical administration for use in the treatment of skin and soft tissue infections and also in the treatment of acne in humans.

Compounds of the present invention may be also used for the elimination or reduction of nasal carriage of pathogenic bacteria such as *S. aureus, H. influenzae, S. pneumonia* and *M. catarrhalis*, in particular colonisation of the nasopharynx by such organisms, by the administration of a compound of the present invention thereto. Accordingly, in a further aspect, the present invention provides for the use of a compound of the invention or a pharmaceutically acceptable salt or derivative or solvate thereof in the manufacture of a medicament adapted for administration to the nasal cavity, for reducing or eliminating the nasal carriage of pathogenic organisms. Preferably, the medicament is adapted for focussed delivery to the nasopharynx, in particular the anterior nasopharynx.

Such reduction or elimination of nasal carriage is believed to be useful in prophylaxis of recurrent acute bacterial sinusitis or recurrent otitis media in humans, in particular in reducing the number of episodes experienced by a patient over a given period of time or increasing the time intervals between episodes. Accordingly, in a further aspect, the present invention provides for the use of a compound of the invention or a pharmaceutically acceptable salt or derivative or solvate thereof in the manufacture of a medicament adapted for administration to the nasal cavity, for prophylaxis of recurrent acute bacterial sinusitis or recurrent otitis media Compounds of the present invention are also useful in treating chronic sinusitis. Accordingly, in a further aspect, the present invention provides for the use of a compound of the invention or a pharmaceutically acceptable salt or derivative or solvate thereof in the manufacture of a medicament, for treating of chronic sinusitis.

The compounds according to the invention may suitably be administered to the patient at a daily dosage of from 1.0 to 50 mg/kg of body weight. For an adult human (of approximately 70 kg body weight), from 50 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

To lessen the risk of encouraging the development of resistant organisms during prophylaxis of recurrent otitis media or recurrent acute bacterial sinusitis, it is preferred to administer the drug on an intermittent, rather than a continual, basis. In a suitable intermittent treatment regimen for prophylaxis of recurrent otitis media or recurrent sinusitis, drug substance is administered on a daily basis, for a small number of days, for instance from 2 to 10, suitably 3 to 8, more suitably about 5 days, the administration then being repeated after an interval, for instance, on a monthly basis over a period of months, for instance up to six months. Less preferably, the drug substance may be administered on a continuing, daily basis, over a prolonged period, for instance several months. Suitably, for prophylaxis of recurrent otitis media or recurrent acute bacterial sinusitis (RABS), drug substance is administered once or twice a day. Suitably, drug substance is administered during the winter months when bacterial infections such as recurrent otitis media and recurrent sinusitis tend to be more prevalent. The drug substance may be administered at a dosage of from 0.05 to 1.00 mg, typically about 0.1 to 0.2 mg, in each nostril, once or twice a day.

More generally, the compounds and compositions according to the invention may be formulated for administration in any convenient way for use in human or veterinary medicine, by analogy with other antibiotics.

Accordingly, in a further aspect, the present invention provides a pharmaceutical composition comprising a compound of the invention or a pharmaceutically acceptable salt or derivative or solvate thereof together with a pharmaceutically acceptable carrier or excipient.

The compounds and compositions according to the invention may be formulated for administration by any route, for example oral, topical or parenteral. The compositions may, for example, be made up in the form of tablets, capsules, powders, granules, lozenges, creams, syrups, sprays or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, nose drops, nasal sprays, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, ethanol or oleyl alcohol for lotions and aqueous bases for sprays. Such carriers may constitute from about 1% to about 98% by weight of the formulation; more usually they will constitute up to about 80% by weight of the formulation.

Compositions according to the invention intended for topical administration, in addition to the above, may also contain a steroidal anti-inflammatory agent; for example, betamethasone.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilised before being filled into a suitable vial or ampoule, which is then sealed. Advantageously, conventional additives including, for example, local anaesthetics, preservatives, and buffering agents can be dissolved in the vehicle. In order to enhance the stability of the solution, the composition may be frozen after being filled into the vial, and the water removed under vacuum; the resulting dry lyophilised powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterisisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

A compound or composition according to the invention is suitably administered to the patient in an anti-microbially effective amount.

A composition according to the invention may suitably contain from 0.001% by weight, preferably (for other than spray compositions) from 10 to 60% by weight, of a compound according to the invention (based on the total weight of the composition), depending on the method of administration.

When the compositions according to the invention are presented in unit dosage form, for instance as a tablet, each unit dose may suitably comprise from 25 to 1000 mg, preferable from 50 to 500 mg, of a compound according to the invention.

Representative compositions of the present invention include those adapted for intranasal administration, in particular, those that will reach into the nasopharynx. Such compositions are preferably adapted for focussed delivery to, and residence within, the nasopharynx. The term 'focussed delivery' is used to mean that the composition is delivered to the nasopharynx, rather than remaining within the nares. The term 'residence' within the nasopharynx is used to mean that the composition, once delivered to the nasopharynx, remains within the nasopharynx over a course of several hours, rather than being washed away more or less immediately. Preferred compositions include spray compositions and creams. Representative aqueous sprays are described in WO 99/21855 (SmithKline Beecham). Representative oily spray and cream compositions are described in WO 98/14189 (SmithKline Beecham).

Suitably, the drug substance is present in compositions for nasal delivery in between 0.001 and 5%, preferably 0.005 and 3%, by weight of the composition. Suitable amounts include 0.5% and 1% by weight of the composition (for oily compositions and creams) and from 0.01 to 0.2% (aqueous compositions).

Spray compositions according to the present invention may be delivered to the nasal cavity by spray devices well known in the art for nasal sprays, for instance an air lift pump. Preferred devices include those that are metered to provide a unit volume of composition, preferably about 100 $\mu$l, and optionally adapted for nasal administration by addition of a modified nozzle.

The invention is illustrated by the following Examples.

EXAMPLES

Intermediate 1

To bis-2-hydroxyethylamine (0.63 g) in THF (30 ml) was added polydimethylaminomethylpolystyrene (3.2 mmol/g, 2.5 g) and methanesulfonyl chloride (0.358 ml), and the mixture stirred for 20 h. The solid was filtered and extracted with THF (4 ml). The combined THF solutions were passed through a 1 g SCX cartridge and evaporated to a colourless gum (0.395 g). NMR analysis indicated a 19:3:10 ratio of N-monosulfonyl:N,O-disulfonyl:N,O,O-trisulfonyl product, which was used without further purification in general procedure A.

Intermediate 2

To 3-hydroxypropylamine (0.45 g) in THF (30 ml) was added polydimethylaminomethylpolystyrene (3.2 mmol/g, 2.5 g) and methanesulfonyl chloride (0.358 ml), and the mixture stirred for 20 h. The solid was filtered and extracted with ThF (4 ml). The combined THF solutions were passed through a 1 g SCX cartridge and evaporated to a colourless gum (0.271 g). NMR analysis indicated a 27:73 ratio of N-monosulfonyl:N,O-disulfonyl product, which was used without further purification in general procedure A.

Intermediate 3

N-(2-hydroxyethyl)oxalamide

Ethyl oxamate (1.17 g, 10 mmol) in methanol (15 ml) was added to aminoethanol (0.732 g, 12 mmol) and the mixture stirred for 3 h. The precipitated product was filtered off, washed with methanol, and dried in vacuo to give the title compound as a white powder (0.94 g, 71%); NMR [(CD$_3$)$_2$SO] 3.18 (2H, q, J=6 Hz), 3.43 (2H, q, J=6 Hz), 4.72 (1H, t, J=6 Hz), 7.75 (1H, br s), 8.03 (1H, br s), and 8.43 (1H, bt).

Intermediate 4

N-(2-Hydroxy-1,1-dimethylethyl)oxalamide

Prepared as in Intermediate 3, using 2-amino-2-methylpropanol. The product did not precipitate out, even on adding diethyl ether. The solution was passed through a SCX cartridge, to remove excess amine, then evaporated to give the title compound as a white powder (1.54 g, 96%); NMR [(CD$_3$)$_2$SO] 1.25 (6H, s), 3.36 (2H,d), 5.07 (1H, t), 7.74 (1H, s), 7.78 (1H, br s), and 8.04 (1H, br s).

Intermediate 5

N-((3S,4R)-4-Hydroxytetrahydrofuran-3-yl)oxalamide

Prepared as in Intermediate 3, using (3R,4S)-4-aminotetrahydrofuran-3-ol hydrochloride [Schaus et al, *J. Org. Chem.*, 62, 4197 (1997)] and triethylamine, to give the title compound as a pale brown powder (1.13 g, 65%); NMR [(CD$_3$)$_2$SO] 3.45–3.56 (2H, m), 3.84–3.94 (2H, m), 3.98–4.01 (1H, m), 4.19–4.24 (1H, m), 5.24 (1H, t), 7.79 (1H, br s), 8.06 (1H, br s), and 8.66 (1H, d).

Intermediate 6

N-(3-hydroxypropyl)oxalamide

Prepared as in Intermediate 3, using 3-aminopropanol to give the title compound as a white powder (1.15 g, 75%); NMR [(CD$_3$)$_2$SO] 1.6 (2H, m), 3.18 (2H, m), 3.42 (2H, m), 4.47 (1H, t), 7.73 (1H, br s), 8.0 (1H, br s), and 8.63 (1H, t).

Intermediate 7

6-Hydroxymethyl-1H-pyridin-2-one

1H-Pyridin-2-one-6-carboxylic acid (2.51 g, 18 mmol) was suspended in dry THF (30 ml) and 1,2-dimethoxyethane (10 ml) under argon. Lithium aluminium hydride (1.0 M in diethyl ether) (30 ml, 30 mmol) was added and the mixture heated to reflux. After 67 h heating was stopped, the mixture cooled to 0° C. and acetic acid (7 ml) added. The solvent was removed in vacuo and the residue purified by flash column chromatography on silica gel, eluting with 20–30% methanol in dichloromethane, to give the title compound as tan needles (0.714 g, 32%); $\delta_H$ (400 MHz; CD$_3$OD) 4.47 (2H, s), 6.38 (1H, d, J 6.8), 6.41 (1H, d, J 9.2), 7.56 (1H, dd, J 6.8, 9.2); m/z J 6.8, 9.2); m/z (ES+) 126 (100%, [MH]$^+$).

Intermediate 8

2,6-Di(bis(tert-butoxycarbonyl)amino)-4-hydroxymethylpyrimidine (a) Methyl 2,6-diaminopyrimidine-4-carboxylate 2,6-Diaminopyrimidine-4-carboxylic acid [Nishigaki et al, *Chem. Pharm. Bull.*, 18, 1003 (1970)](3.27 g, 21 mmol) was suspended in methanol (200 ml) which had been saturated with hydrogen chloride. The mixture was refluxed for 5 h then evaporated to dryness to give the crude title compound (3.53 g, 100%).

(b) Methyl 2,6-di(bis(tert-butoxycarbonyl)amino) pyrimidine-4-carboxylate Crude methyl 2,6-diaminopyrimidine-4-carboxylate (2.52 g, 15 mmol) was suspended in dry tetrahydrofuran (200 ml) then treated sequentially with di-tert-butyl dicarbonate (19.6 g, 90 mmol), triethylamine (16.7 ml, 120 mmol), and 4 dimethylaminopyridine (0.092 g, 0.75 mmol). This mixture was refluxed gently for 16 h, evaporated, dissolved in diethyl ether, washed with water and brine, dried and evaporated to give a dark red gum. This residue was purified by flash chromatography, eluting with 0–18% ethyl acetate in petroleum ether, to give the title compound as an off-white foam (4.58 g, 54%); m/z (APCI+) 569 [MH]$^+$100%.

(c) 2,6-Di(bis(tert-butoxycarbonyl)amino)-4-hydroxymethylpyrimidine Methyl 2,6-di(bis(tert-butoxycarbonyl)amino)pyrimidine-4-carboxylate (0.284 g, 0.5 mmol) was dissolved in tetrahydrofuran (4.5 ml) and water (0.5 ml) then sodium borohydride (0.038 g, 1 mmol) added. The mixture was stirred for 0.5 h, then diluted with ethyl acetate, washed with dilute sodium chloride solution and brine, dried and evaporated to give the crude product as a white foam. This was purified by flash chromatography, eluting with 15–30% ethyl acetate in petroleum ether, to give the title compound as a white foam (0.183 g, 68%); LC/MS (APCI+) 541 [MH]$^+$100%.

Intermediate 9

5-Hydroxymethylpyrazine-2-carboxylic Acid Amide

Pyrazinecarboxylic acid amide (0.492 g, 4 mmol) was suspended in methanol (8 ml), water (4 ml) and concentrated sulphuric acid (0.22 ml, 4 mmol), then iron (II) sulphate heptahydrate (0.334 g, 1.2 mmol) was added and the mixture degassed. To this was then added hydroxylamine-O-sulphonic acid (1.36 g, 12 mmol). After 6 h more sulphuric acid and iron (II) sulphate heptahydrate were added. After a further 1 h the mixture was adjusted to pH 7, evaporated, and the residue extracted with methanol. This solution was pre-absorbed onto silica then purified by chromatography, eluting with 0–10% '2 M ammonia in methanol' in dichloromethane, to give the title compound as an off-white solid (0.102 g, 17%); NMR [(CD$_3$)$_2$SO] 4.72 (2H, d), 5.72 (1H, t), 7.79 (1H, br s), 8.22 (1H, br s), 8.73 (1H, d), and 9.09 (1H, d).

Intermediate 10

4-Amino-5-cyano-2-hydroxymethylpyrimidine

To hydroxyacetamidine hydrochloride (3.3 g) in ethanol (40 ml) was added ethanolic sodium ethoxide prepared from ethanol (25 ml) and sodium (0.76 g). The sodium chloride was filtered off and the solution added to ethoxymethylene malondinitrile (3.66 g) in ethanol (30 ml). After 1 h the precipitated orange title product was removed by filtration (2.27 g, 45%); NMR [(CD$_3$)$_2$SO] 4.4 (d, J=6.2 Hz, 2H), 5.1 (t, J=6.2 Hz, 1H), 7.9 (bs, 1H), 8.6 (s, 1H).

Intermediate 11

4-Amino-5-cyano-2-hydroxymethyl-6-methylpyrimidine

To hydroxyacetamidine hydrochloride (3.3 g) in ethanol (40 ml) was added ethanolic sodium ethoxide prepared from ethanol (25 ml) and sodium (0.76 g). The sodium chloride was filtered off and the solution added to 1-ethoxyethylene malondinitrile (4.08 g) in ethanol (30 ml). After 1 h the precipitated yellow title product was removed by filtration (4.29 g, 75%); NMR [(CD$_3$)$_2$SO] 2.4 (3H, s), 4.3 (d, J=6.1 Hz, 2H), 5.0 (t, J=6.1 Hz, 1H), 7.7 (bs, 1H). 7.7 (bs, 1H).

Intermediate 12

4-Amino-5-(N-Boc-aminomethyl)-2-hydroxymethylpyrimidine

To the compound of Intermediate 10 (1.5 g) in THF (180 ml) under argon was added 1 M lithium aluminium hydride in THF (20 ml) and the reaction stirred at 20° C. for 24 h. Water (1.5 ml) in THF (10 ml) was added dropwise and the precipitated solid filtered off and extracted with ethanol. The combined solutions were evaporated to dryness under reduced pressure and the residue taken up in water (50 ml) and treated with di-t-butyl dicarbonate (5 g) in THF (50 ml). The mixture was stirred for 24 h, then extracted with ethyl acetate. The extract was washed with brine, dried and evaporated to a yellow gum which was purified by chromatography on silica eluting with ethyl acetate to give the title product as a yellow gum (0.41 g, 26%); NMR (CDCl$_3$) 1.45 (s, 9H), 4.2 (d, J=6.8 Hz, 2H), 4.55 (s, 2H), 4.95 (bt, 1H), 6.1 (bs, 2H), 8.0 (s, 1H).

Intermediate 13

3-Hydroxy-3-methylpyrrolidine-1-carboxylic Acid Tert-butyl Ester

3-Oxo-pyrrolidine-1-carboxylic acid tert-butyl ester [Hofmann, *J. Agric. Food Chem.*, 46, 3902 (1998)] (0.322 g, 1.74 mmol) was dissolved in diethyl ether (5 ml), cooled with an ice bath, and treated with methylmagnesium bromide (3M in ether, 0.64 ml, 1.91 mmol). The reaction was stirred for 1 h then more methylmagnesium bromide added, and the mixture stirred for 63 h. The reaction was quenched with aqueous ammonium chloride and extracted with diethyl ether (x3). The combined organic extracts were dried and evaporated. The residue was purified by flash chromatography, eluting with 0–50% ethyl acetate in petroleum ether, to give the title compound as a sticky off-white solid (0.129 g, 37%); NMR (CDCl$_3$) 1.41 (3H, s), 1.46 (9H, s), 1.61 (1H, s), 1.79–1.92 (2H, m), and 3.17–3.58 (4H, m).

Intermediate 14

N-Boc-(2S,4R)-4-Hydroxypyrrolidine-2-carboxamide

To Boc-hydroxyproline dicyclohexylamine salt (8.25 g) in acetonitile (25 ml) was added di-t-butyl dicarbonate (6 g), pyridine (1 ml) and ammonium bicarbonate (2 g). After stirring at 20° C. for 24 h, the mixture was diluted with water (50 ml) and extracted twice with ethyl acetate (100+50 ml). The organic extracts were combined, dried and evaporated to give a colourless foam (6.1 g), which was shown to be highly impure. A third extraction of the aq layer with ethyl acetate (100 ml) gave the title product as a white foam, (1.5 g). NMR [(CD$_3$)$_2$SO] major rotamer: 1.34, (s, 9H), 1.8 (m, 1H), 2.0 (m, 1H), 3.23 (m, 1H), 3.37(m, 1H), 4.08 (m, 1H), 4.21 (m, 1H), 4.95 (d, 3.2 Hz, 1H), 6.88 (bs, 1H), 7.33 (bs, 1H); minor rotamer: 1.39 (s, 9H), 1.8 (m, 1H), 2.0 (m, 1H), 3.23 (m, 1H), 3.37(m, 1H), 4.08 (m, 1H), 4.21 (m, 1H), 4.95 (d, 3.2 Hz, 1H), 6.81 (bs, 1H), 7.3 (bs, 1H).

Intermediate 15

N-Boc-(2S,3S)-3-Hydroxypyrrolidine-2-carboxamide

To N-Boc-(2S,3S)-3-hydroxypyrrolidine-2-carboxylic acid (1.36 g) in DMF (6 ml) added ammonium bicarbonate (0.5 g) and dicyclohexylcarbodiimide (1.3 g). After stirring at 20° C. for 20 h the reaction was concentrated by evaporation under reduced pressure, and the residue triturated with ethyl acetate. The soluble material was purified by chromatography on silica eluting with 50–100% (5% acetic acid in diethyl ether) in hexane to give the title material as a colourless gum, (0.5 g). NMR (CD$_3$OD) major rotamer: 1.43, (s, 9H), 1.88 (m, 1H), 2.0 (m, 1H), 3.55 (m, 2H), 4.03(s, 1H), 4.31 (bs, 1H); minor rotamer: 1.47, (s, 9H), 1.7 (m, 1H), 2.0 (m, 1H), 3.55 (m, 2H), 4.09(s, 1H), 4.34 (d, J=4 Hz, 1H).

Intermediate 16

N-Boc-(2S,4R)-4-Hydroxy-2-t-butyldimethylsilyloxymethylpyrrolidine

To N-Boc-(2S,4R)-4-hydroxy-2-hydroxymethylpyrrolidine (0.199 g, 0.92 mmol) in DMF (2 ml) was added imidazole (0.125 g) and t-butyldimethylsilyl chloride (0.14 g). After 1.5 h, the reaction was concentrated by evaporation under reduced pressure, and the residue dissolved in diethyl ether, washed with water and brine, dried and evaporated. Purification by chromatography on silica gel eluting with 0–30% ethyl acetate in hexane gave the title material, (0.15 g, 49%). NMR (CDCl$_3$) 0.02 (s, 3H), 0.03 (s, 3H), 0.9 (s, 9H), 1.45 (s, 9H), 1.9 (bm, 9H), 2.2 (bm, 1H), 3.3–4.0 (bm, 5H), 4.5 (m, 1H).

Intermediate 17

N-Boc-(2S,4R)-2-Carbamoylmethyl-4-hydroxypyrrolidine

To N-Boc-(2S,4R)-4-hydroxy-2-hydroxymethylpyrrolidine (0.105 g in THF (5 ml) cooled to 0° C. under argon was added carbonyl diimidazole (121 mg). After 3 h aqueous ammonia (20 M, 0.25 ml) was added and the reaction stirred for 17 h. The reaction mixture was evaporated to dryness under reduced pressure and the residue purified by chromatography on silica eluting with 80–100% ethyl acetate in hexane to give the title product as a colourless gum (45 mg, 31%); NMR (CDCl$_3$) 1.47 (s, 9H), 2.05 (m, 3H), 3.4–3.6 (m, 2H), 4.154.3 (m, 3H), 4.45 (m, 1H), 4.75 (bs, 2H).

Intermediate 18

N-Boc-Isoxazolidin-4-ol

Isoxazolidin-4-ol hydrochloride (0.1 g) in dichloromethane (2 ml) was treated with triethylamine (0.14 ml) and di-t-butyl dicarbonate (0.22 g). The reaction was stirred at 20° C. for 18 h. The reaction mixture was washed with water, 5% aqueous citric acid and brine, dried and evaporated to a colourless gum. Purification by chromatography on silica gel eluting with 0–100% ethyl acetate in hexane gave the title material, (0.15 g, 49%). NMR (CDCl$_3$) 1.5 (s, 9H), 3.68 (dd, J=2 Hz, 12 Hz, 1H), 3.73 (dd, J=5 Hz, 12 Hz, 1H), 3.94 (d, J=3 Hz, 2H), 4.76 (m, 1H).

Intermediate 19

(3R,3aR,6S,6aR)-6-azido-hexahydrofuro[3,2-b]furan-3-ol (a) (3R,3aS,6R,6aR)-6-Hydroxy-hexahydro-furo[3,2-b]furan 3-O-methanesulfonate (3R,3a,6R,6aR)-Hexahydrofuro[3,2-b]furan-3,6-diol (3.21 g, 22 mmol) was dissolved in dry dichloromethane (100 ml), cooled in an ice/salt bath and treated sequentially with triethylamine (3.35 ml, 24 mmol) and methanesulfonyl chloride (1.55 ml, 20 mmol). The mixture was stirred for 20 h while warming to room temperature. The solution was washed with water then brine, dried and evaporated to give a brown oil (2.9 g). This residue was purified by flash chromatography, eluting with 0–8% methanol in dichloromethane, to give the title compound as an off-white gum (1.35 g, 35%).

(b) (3R,3aR,6S,6aR)-6-azido-hexahydrofuro[3,2-b]furan-3-ol (3R,3aS,6R,6Hydroxy-hexahydro-furan[3,2-b]furan 3-O-methanesulfonate (0.768 g, 4 mmol) was dissolved in dry dimethylformamide (8 ml) then sodium azide (0.325 g, 5 mmol) added. The mixture was heated at 55° C. for 20 h, 75° C. for 2 h, 110° C. for 24 h and 120° C. for 48 h. Water was then added and Water was then added and the mixture extracted with ethyl acetate. The combined organic extracts were dried and evaporated to give a pale orange solid (0.5 g). This residue was purified by flash chromatography, eluting with 30–70% ethyl acetate in petroleum ether, to give the title compound as a colourless solid (0.346 g, 51%); NMR (CDCl$_3$) 2.55 (1H, d), 3.60 (1H, dd), 3.87 (1H, dd), 3.97 (1H, dd), 4.08 (2H, m), 4.32 (1H, m), 4.47 (1H, d), and 4.63 (1H, m).

Intermediate 20

(S)-3-Hydroxy-4-methoxyimino-pyrrolidine-1-carboxylic acid tert-butyl Ester (a) 3a, 7a-dihydroxy-octahydro-4,8-dioxa-2,6-diaza-s-indacene-2,6-dicarboxylic acid di-tert-butyl ester Dimethyl sulfoxide (279 µl, 3.94 mmol) was added dropwise to a stirred solution of oxalyl chloride (258 µl, 2.95 mmol) in THF (10 ml) at −78° C. After 10 min (3S,4S)-3,4-dihydroxy-pyrrolidine-1-carboxylic acid tert-butyl ester (0.5 g, 2.46 mmol) [Nagel, *Angew. Chem.*, 96, 425 (1984)] in THF (5 ml) was added. The mixture was stirred at −78° C. for 95 min, after which triethylamine (1.7 ml, 12.3 mmol) was added. Stirring was continued for a further 20 min, after which the mixture was allowed to warm to room temperature. Citric acid (5% solution) (20 ml) was added and the mixture extracted with ethyl acetate. The organic extracts were combined, dried (MgSO$_4$), filtered, and concentrated in vacuo then purified by flash column chromatography on silica gel, eluting with 50–70% ethyl acetate in petroleum ether to give 3a, 7a-dihydroxy-octahydro-4,8-dioxa-2,6-diaza-s-indacene-2,6-dicarboxylic acid di-tert-butyl ester (195 mg, 20%); m/z (ES+) 425 (100%, [MNa]$^+$).

(b) (S)-3-Hydroxy-4-methoxyimino-pyrrolidine-1-carboxylic acid tert-butyl ester To 3a, 7a-dihydroxy-octahydro-4,8-dioxa-2,6-diaza-s-indacene-2,6-dicarboxylic acid di-tert-butyl ester (188 mg, 0.47 mmol) in DCM (10 ml) was added methoxylamine hydrochloride (94 mg, 1.12 mmol), followed by triethylamine (157 µl, 1.12 mmol). After stirring at room temperature for 44 hours the mixture was concentrated in vacuo then purified by flash column chromatrography on silica gel, eluting with 20–30% ethyl acetate in petroleum ether to give the title compound as a white solid (156 mg, 73%); $\delta_H$ (400 MHz; CDCl$_3$) 1.47 (9H, s), 2.87 (1H, d), 3.43–3.50 (1H, m), 3.72–3.83 (1H, br m), 3.92 (3H, s), 4.12 (2H, AB q), 4.70–4.75 (1H, m); m/z (ES+) 253 (87%, [MNa]$^+$), 157 (100%).

Intermediate 21

1-Hydroxycyclopropanecarboxamide

To 1-hydroxycyclopropanecarboxylic acid (0.20 g, 1.96 mmol) in dry DMF (15 ml) was added 1-hydroxy-7-azabenzotriazole (0.27 g, 2.15 mmol). Ammonia (0.037 g, 2.15 mmol) was added, followed by 1-[3-(dimethylamino) propyl]-3-ethylcarbodiimide hydrochloride (0.38 g, 2.15 mmol) after 30 min. The mixture was stirred under argon for 68 h, water (1 ml) was added, and the mixture concentrated in vacuo. The residue was taken up in sodium hydrogen carbonate solution (1 ml), filtered through hydromatrix gel and washed through with ethyl acetate. The filtrate was concentrated in vacuo then purified by flash column chromatography on silica gel, eluting with ethyl acetate to give the title compound as a colourless solid (0.048 g, 24%); $\delta_H$ (400 MHz; CD$_3$OD) 0.94–0.98 (2H, m), 1.18–1.21 (2H, m).

Intermediate 22

1-Dimethylaminomethylcyclopropanol Hydrochloride (a) 1-Hydroxycyclopropanecarboxylic acid dimethylamide To 1-hydroxycyclopropanecarboxylic acid (1.20 g, 1.8 mmol) in dry DMF (15 ml) was added 1-hydroxy-7-azabenzotriazole (1.76 g, 12.9 mmol). Dimethylamine in THF (2.0 M; 6.5 ml, 12.9 mmol) was added, followed by 1-[3-(dimethylamino)propyl]-3-ethylcarbodiimide hydrochloride (2.48 g, 12.9 mmol) after 30 min. The mixture was stirred under argon for 22 h, water (2 ml) was added, and the mixture concentrated in vacuo. The residue was taken up in sodium hydrogen carbonate solution and extracted with ethyl acetate. The organic extracts were combined, dried (MgSO$_4$), filtered, and concentrated in vacuo then purified by flash column chromatography on silica gel, eluting with 90–100% ethyl acetate in petroleum ether to give 1-hydroxycyclopropanecarboxylic acid dimethylamide as a colourless solid (1.15 g, 76%); $\delta_H$ (400 MHz; CDCl$_3$) 0.91–0.94 (2H, m), 1.03–1.06 (2H, m), 3.11 (6H, br s), 4.53 (1H, br s); m/z (ES+) 130 (100%, [MH]$^+$).

(b) 1-(Dimethylaminomethyl)cyclopropanol hydrochloride A solution of 1-hydroxycyclopropanecarboxylic acid dimethylamide (435 mg, 3.4 mmol) in diethyl ether (15 ml) was cooled in an ice bath. Lithium aluminium hydride (1.0 M in diethyl ether; 8.4 ml, 8.4 mmol) was added and the mixture heated to reflux. After 3 h sodium hydroxide solution (40%; 2 ml) was added to the ice-cooled mixture. The precipitate which formed was filtered off and washed with ethyl acetate. The filtrate was dried (MgSO$_4$), filtered, acidified with methanolic hydrogen chloride, then concentrated in vacuo to give the title compound as a colourless solid (466 mg, 91%); $\delta_H$ (400 MHz; CD$_3$OD) 0.73–0.76 (2H, m), 0.90–0.93 (2H, m), 2.96 (6H, s), 3.26 (2H, s); m/z (ES+) 116 (100%, [MH]$^+$).

Intermediates 23 and 24

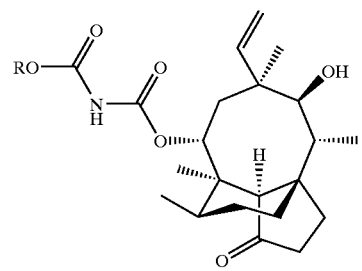

Intermediates 23 and 24 were prepared by general procedure A. The crude reaction was suspended in dilute sodium hydrogen carbonate solution and extracted with ethyl acetate. The aqueous was acidified with hydrochloric acid (2 M) and extracted with ethyl acetate. The combined organic extracts were dried (MgSO$_4$), filtered, and concentrated in vacuo.

| Int. | R | Alcohol | MW | Yield | LC/MS |
|---|---|---|---|---|---|
| 23 | HO-C(=O)-CH$_2$-* | Ref A, * | 465 | 72% | 488 (ES$^+$) [MNa]$^+$ 20% |
| 24 | HO-C(=O)-C(Me)(Me)-* | C, * | 493 | 67% | 516 (ES$^+$) [MNa]$^+$ 35% |

* Starting alcohol is t-butyl ester.

References
Reference A: Juraj and Cushman, *Tetrahedron*, 48, 8601 (1992).

Intermediate 25

(3R,4S)-4-Boc-amino-3-hydroxytetrahydrofuran (3R,4S)-4-Amino-3-hydroxytetrahydrofuran hydrochloride (Scott et al, *J. Org. Chem.*, 62, 4197 (1997); 0.75 g, 5.37 mmol) in dichloromethane (10 ml) was treated with triethylamine (0.8 ml) and t-butyl dicarbonate (1.3 g). The reaction was stirred at 20° C. for 18 h. The reaction mixture was diluted with ether (20 ml) washed with water, 5% aqueous citric acid and brine, dried and partially evaporated under reduced pressure, to give a white solid. This was collected, washed with hexane and dried under reduced pressure to give the title compound, (0.64 g, 58%). NMR (CDCl$_3$) 1.45 (9H, s), 3.0 (1H, bs), 3.6 (1H, dd), 3.7 (1H, dd), 3.95 (1H, m), 4.1 (2H, m), 4.28 (1H, m), 4.7 (1H, bm).

Example 1

Mutilin 14-[N-(2-methylsulfonylethoxycarbonyl)] carbamate (a) (3R)-3-Deoxo-11-deoxy-3-methoxy-11-oxo-4-epimutilin 14-[N-(2-methylsulfonylethoxycarbonyl)] carbamate 2-(Methylsulfonyl)ethyl chloroformate (Wolters et al., Synthesis 563, 1996; 0.41 g, 2.2 mmol) was dissolved in dry dichloromethane (10 ml) then silver cyanate (0.495 g, 3.3 mmol) added. After stirring for a few minutes (3R)-3-deoxo-11-deoxy-3-methoxy-11-oxo-4-epimutilin (0.668 g, 2 mmol) was added, and stirring continued for 2.5 h. The mixture was then filtered through kieselguhr and evaporated. The residue was purified by flash chromatography, eluting with 0–50% ethyl acetate in petroleum ether, to give (3R)-3-deoxo-11-deoxy-3-methoxy-11-oxo-4-epimutilin 14-[N-(2-methylsulfonylethoxycarbonyl)]carbamate (0.78 g, 74%); LC/MS (APCI–) 526 (100%, [M–H]$^-$).

(b) Mutilin 14-[N-(2-methylsulfonylethoxycarbonyl)] carbamate. (3R)-3-Deoxo-11-deoxy-3-methoxy-11-oxo-4-epimutilin 14-[N-(2-methylsulfonylethoxycarbonyl)] carbamate (0.468 g, 0.89 mmol) was dissolved in 1,4-dioxane (12 ml) and cooled to 5–10° C. Lukas reagent (3 ml) was then added and the mixture stirred for 4.5 h with cooling and for 3 h at room temperature. The mixture was diluted with ethyl acetate, washed with water (x2), saturated sodium hydrogen carbonate, and brine, dried and evaporated. The residue was purified by flash chromatography, eluting with 40–80% ethyl acetate in petroleum ether, to give the title compound as a white foam (0.362 g, 79%); LC/MS (APCI–) 512 (100%, [M–H]$^-$).

General Procedure A, for the Preparation of Mutilin 14-[N-(alkoxycarbonyl)]carbamates (3R)-3-Deoxo-11-deoxy-3-methoxy-11-oxo-4-epimutilin 14-chloroformate (WO 97/25309; 0.16 g, 0.4 mmol) was dissolved in dry dichloromethane (2.5 ml) and added to silver cyanate (0.09 g, 0.6 mmol). To this stirred suspension was added pyridine (0.008 g, 0.1 mmol) in dry dichloromethane (0.1 ml). After 1.5 min the appropriate alcohol (ca 1 equiv. for mono-alcohols or 2–7.5 equiv. for diols) in dry dichloromethane or DMF was added. The mixture was stirred for 3.5 h then filtered through kieselguhr and evaporated. The residue was dissolved in 1,4-dioxane (4 ml), concentrated hydrochloric acid (2 ml) added, and the mixture stirred for 6 h. After evaporation the residue was suspended in dilute sodium hydrogen carbonate solution and extracted with ethyl acetate (x2). The combined organic extracts were washed with brine, dried and evaporated. The residue was purified by column chromatography on silica gel, eluting with 20–100% ethyl acetate in petroleum ether then 3–4% methanol in ethyl acetate, to give the required product.

Examples 2–6

Examples 2–6 were prepared by general procedure A.

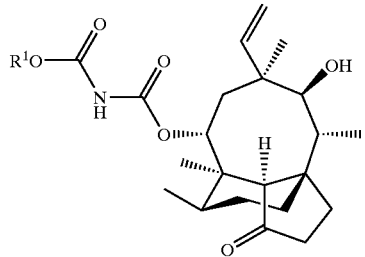

| Example | R$^1$ | MW | Yield | LC/MS (APCI–) [M – H]$^-$ |
|---|---|---|---|---|
| 2 | Me | 421 | 21% | 420, 100% |
| 3 | HO(CH$_2$)$_2$— | 451 | 31% | 450, 100% |
| 4 | HO-(pyridinyl)-CH$_2$— | 528 | 11% | 527, 100% |
| 5 | H$_2$N-C(=O)-CH(Me)— | 478 | 29% | 477, 100% |
| 6 | Me-C(=O)-NH-CH$_2$CH$_2$CH$_2$— | 492 | 71% | 491, 100% |

Examples 7–68

Examples 7–68 were prepared by general procedure A. For basic products the aqueous work-up was omitted and the residue was purified by column chromatography on silica gel eluting with 0–15% 2M methanolic ammonia in dichloromethane. The alcohol starting material was commercially available unless otherwise indicated.

| Example | R | Alcohol | MW | Yield | LC/MS |
|---|---|---|---|---|---|
| 7 | (H₂N-C(=O)-CH₂-C(CH₃)₂-) | C | 464 | 56% | 463 (APCI−) [M − H]⁻ 100% |
| 8 | Me-S(O)₂-NH-CH₂CH₂-C(CH₃)₂- | Ref 1 | 528 | 30% | 527 (APCI−) [M − H]⁻ 100% |
| 9 | Me-S(O)₂-N((CH₂)₂OH)-CH₂CH₂-C(CH₃)₂- | Int. 1 | 572 | 13% | 571 (APCI−) [M − H]⁻ 100% |
| 10 | Me-S(O)₂-NH-CH₂CH₂CH₂-C(CH₃)₂- | Int. 2 | 542 | 17% | 565 (APCI+) [MNa]⁺ 100% |
| 11 | H₂N-C(=O)-C(=O)-NH-CH₂CH₂-C(CH₃)₂- | Int. 3 | 521 | 46% | 520 (APCI−) [M − H]⁻ 100% |
| 12 | H₂N-C(=O)-C(=O)-NH-C(Me)₂-C(CH₃)₂- | Int. 4 | 549 | 13% | 572 (ES+) (MNa+) 100% |
| 13 | H₂N-C(=O)-C(=O)-NH-(tetrahydrofuranyl)-C(CH₃)- | Int. 5 | 563 | 9% | 586 (ES+) (MNa+) 100% |
| 14 | HO(CH₂)₂NH-C(=O)-C(=O)-NH-CH₂CH₂-C(CH₃)₂- | C | 565 | 33% | 588 (ES+) (MNa+) 100% |

-continued
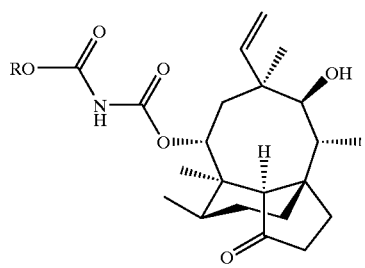
| Example | R | Alcohol | MW | Yield | LC/MS |
|---|---|---|---|---|---|
| 15 | H2N-C(=O)-C(=O)-NH-(CH2)3-C(Me)2- (dashed) | Int. 6 | 535 | 40% | 534 (APCI−) [M − H]⁻ 100% |
| 16 | H2N-C(=O)-O-CH2-CH2-C(Me)2- | Ref 2 | 494 | 59% | 493 (APCI−) [M − H]⁻ 100% |
| 17 | H2N-C(=O)-O-CH2-CH(Me)-C(Me)2- | Ref 3 | 508 | 7% | 507 (APCI−) [M − H]⁻ 100% |
| 18 | H2N-C(=O)-O-CH(Me)-CH(Me)-C(Me)2- | Ref 3 | 522 | 48% | 521 (APCI−) [M − H]⁻ 50% |
| 19 | H2N-C(=O)-O-CH(Me)-CH(Me)-C(Me)2- | Ref 3 | 522 | 45% | 521 (APCI−) [M − H]⁻ 50% |
| 20 | HO-CH2-CH(OH)-CH2-C(Me)2- | C | 481 | 47% | 480 (APCI−) [M − H]⁻ 100% |
| 21 | HO-CH2-CF2-C(Me)2- | Ref 4 | 501 | 59% | 524 (ES+) (MNa+) 100% |
| 22 | H2N-C(=O)-CH(Me)-C(Me)2- | C | 478 | 31% | 477 (APCI−) [M − H]⁻ 100% |
| 23 | tetrahydrothiophene-1,1-dioxide-3-yl | C | 525 | 10% | 524 (APCI−) [M − H]⁻ 100% |

-continued
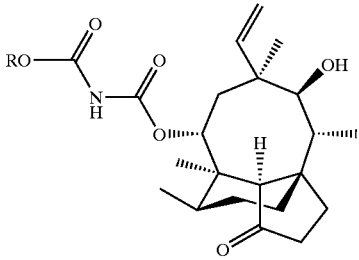
| Example | R | Alcohol | MW | Yield | LC/MS |
|---|---|---|---|---|---|
| 24 | 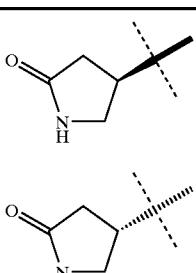 | C | 490 | 25% | 489 (APCI−) [M − H]− 100% |
| 25 | 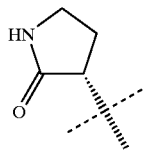 | C | 490 | 9% | 489 (APCI−) [M − H]− 100% |
| 26 | 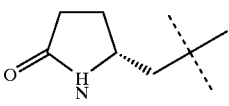 | Ref 5 | 490 | 26% | 513 (ES+) [MNa]+ 100% |
| 27 | 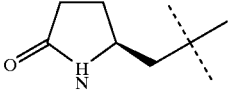 | C | 504 | 55% | 503 (APCI−) [M − H]− 100% |
| 28 | 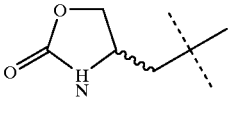 | C | 504 | 42% | 503 (APCI−) [M − H]− 100% |
| 29 | 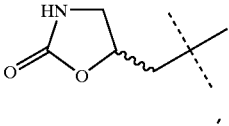 | Ref 6 | 506 | 44% | 505 (APCI−) [M − H]− 100% |
| 30 | 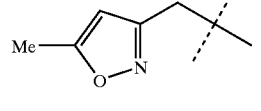 | Ref 7 | 506 | 43% | 505 (APCI−) [M − H]− 100% |
| 31 | 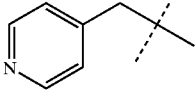 | C | 502 | 55% | 501 (APCI−) [M − H]− 100% |
| 32 | 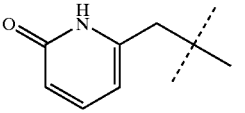 | C | 498 | 31% | 497 (APCI−) [M − H]− 100% |
| 33 |  | Int. 7 | 514 | 13% | 515 (ES+) [MH]+ 100% |

-continued

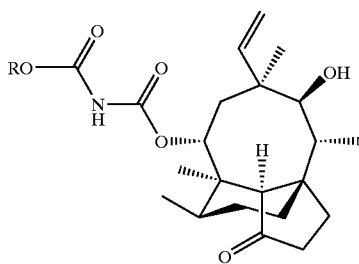

| Example | R | Alcohol | MW | Yield | LC/MS |
|---|---|---|---|---|---|
| 34 | 2,6-diamino-pyrimidin-4-ylmethyl (H₂N-pyrimidine-NH₂) | Int. 8 | 529 | 68% | 530 (ES+) (MH+) 100% |
| 35 | 5-carbamoyl-pyrazin-2-ylmethyl (H₂N-CO-pyrazine) | Int. 9 | 542 | 20% | 541 (APCI−) [M − H]⁻ 40% |
| 36 | 3-carbamoyl-pyrazin-2-ylmethyl (pyrazine-CONH₂) | Ref 8 | 542 | 11% | 541 (APCI−) [M − H]⁻ 60% |
| 37 | 4-amino-5-cyano-pyrimidin-2-ylmethyl | Int. 10 | 539 | 44% | 603 (ES+) [MNa.MeCN]⁺ 100% |
| 38 | 4-amino-5-cyano-6-methyl-pyrimidin-2-ylmethyl | Int. 11 | 553 | 43% | 617 (ES+) [MNa.MeCN]⁺ 100% |
| 39 | 4-amino-5-aminomethyl-pyrimidin-2-ylmethyl | Int. 12 | 543 | 21% | 544 (ES+) [MH]⁺ 100% |
| 40 | 3-methyl-5-hydroxy-pyrazol-4-yl-propyl | C | 531 | 14% | 530 (APCI−) [M − H]⁻ 100% |
| 41 | 6-methyl-2,4-dioxo-pyrimidin-1-yl-propyl | C | 559 | 25% | 558 (APCI−) [M − H]⁻ 100% |

-continued

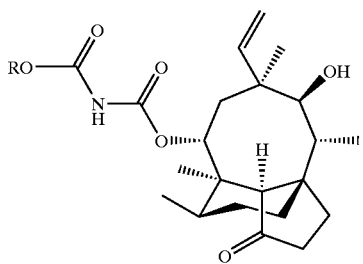

| Example | R | Alcohol | MW | Yield | LC/MS |
|---|---|---|---|---|---|
| 42 | 2-pyridyl-CH(CH₂OH)-C(CH₃)₂- | C | 542 | 37% | 541 (APCI−) [M − H]⁻ 100% |
| 43 | 3-azetidinyl-C(CH₃)₂- (HCl salt) | Ref 9, # | 462 | 66% | 463 (ES+) [MH]⁺ 100% |
| 44 | 3-pyrrolidinyl-CH(CH₃)- | Ref 10, # | 476 | 29% | 475 (ES−) [M − H]⁻ 100% |
| 45 | 3-pyrrolidinyl-CH(CH₃)- | Ref 10, # | 476 | 16% | 475 (ES−) [M − H]⁻ 100% |
| 46 | 3-piperidinyl- | C, # | 490 | 53 | 489 (APCI−) [M − H]⁻ 100% |
| 47 | 4-piperidinyl-C(CH₃)₂- (HCl salt) | Ref 9, # | 490 | 70% | 491 (ES+) [MH]⁺ 100% |
| 48 | 3-methyl-3-pyrrolidinyl-C(CH₃)- | Int. 13, # | 490 | 67% | 489 (APCI−) [M − H]⁻ 100% |
| 49 | trans-3,4-dimethylpyrrolidin-3-yl- (HCl salt, trans racemic) | Ref 11, # | 490 | 34% | 491 (ES+) [MN]⁺ 100% |

-continued
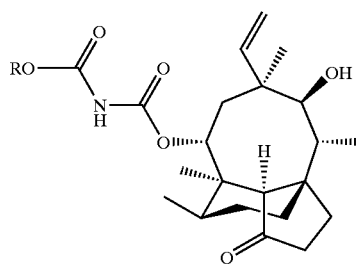
| Example | R | Alcohol | MW | Yield | LC/MS |
|---|---|---|---|---|---|
| 50 | MeO-[pyrrolidine], HCl salt, trans racemic | Ref 12, # | 506 | 58% | 507 (ES+) [MH]⁺ 100% |
| 51 | HO-[pyrrolidine] | Ref 13, # | 506 | 62% | 505 (APCI−) [M − H]⁻ 100% |
| 52 | H₂N-C(O)-[pyrrolidine] | Int. 14, # | 519 | 2% | 518 (ES−) [M − H]⁻ 100% |
| 53 | [pyrrolidine]-C(O)NH₂ | Int. 15, # | 519 | 5% | 518 (ES−) [M − H]⁻ 100% |
| 54 | HO-[pyrrolidine] | Int. 16, # | 506 | 26% | 505 (ES−) [M − H]⁻ 100% |
| 55 | H₂N-C(O)-O-CH₂-[pyrrolidine] | Int. 17, # | 549 | 28% | 548 (ES−) [M − H]⁻ 100% |
| 56 | [isoxazolidine] | Int. 18, # | 478 | 34% | 501 (ES+) [MNa]⁺ 100% |
| 57 | [morpholine], HCl salt | Ref 14, # | 506 | 82% | 507 (ES+) [MH]⁺ 100% |

-continued

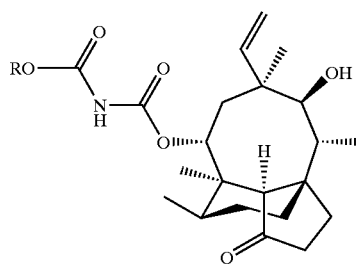

| Example | R | Alcohol | MW | Yield | LC/MS |
|---|---|---|---|---|---|
| 58 | Me$_2$N-CH$_2$CH$_2$-C(Me)$_2$- | C | 478 | 66% | 479 (ES+) (MH$^+$) 100% |
| 59 | HO-CH$_2$CH$_2$-N(Me)-CH$_2$CH$_2$-C(Me)$_2$- | C | 508 | 11% | 507 (ES−) [M − H]$^-$ 100% |
| 60 | (HOCH$_2$CH$_2$)$_2$N-CH$_2$CH$_2$-C(Me)$_2$- | C | 538 | 7% | 539 (ES−) [M − H]$^-$ 100% |
| 61 | Me$_2$N-CH$_2$-CH(Me)-C(Me)$_2$- | C | 492 | 62% | 491 (APCI−) [M − H]$^-$ 100% |
| 62 | Me$_2$N-CH$_2$-CH(OH)-C(Me)$_2$- | C, @ | 508 | 3% | 507 (ES−) [M − H]$^-$ 100% |
| 63 | Me$_2$N-CH$_2$-CH(OH)-C(Me)$_2$- | C, @ | 508 | 30% | 507 (ES−) [M − H]$^-$ 100% |
| 64 | morpholino-CH$_2$-CH(OH)-C(Me)$_2$- | C | 550 | 14% | 549 (ES−) [M − H]$^-$ 100% |
| 65 | piperazinyl-CH$_2$CH$_2$-C(Me)$_2$- | C, # | 519 | 79% | 518 (APCI−) [M − H]$^-$ 100% |
| 66 | morpholino-CH$_2$CH$_2$-C(Me)$_2$- | C | 520 | 24% | 519 (ES−) [M − H]$^-$ 100% |
| 67 | (1,1-dioxo-thiomorpholino)-CH$_2$CH$_2$-C(Me)$_2$- | C | 568 | 20% | 591 (ES+) [MNa]$^+$ 100% |

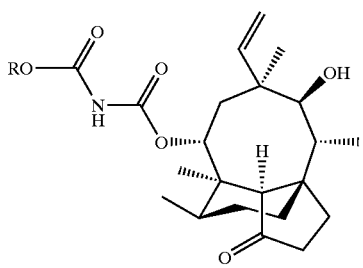

| Example | R | Alcohol | MW | Yield | LC/MS |
|---|---|---|---|---|---|
| 68 | (piperidine-4-carboxamide-N-ethyl group, H₂N-C(O)-piperidine-N-CH₂CH₂-) | C | 561 | 2% | 560 (ES−) [M − H]⁻ 100% |

C commercially available alcohol;
Starting alcohol is N-Boc derivative;
@ both examples isolated from the reaction of the diol.

References:
1. Japan Kokai, JP50149622 (1975).
2. Gormley et al, J. Org. Chem., 45, 1450 (1980).
3. Najer et al, Bull. Soc. Chim. Fr., 1142 (1954).
4. Starrett et al. J. Med. Chem., 37, 1857 (1994).
5. Bentley et al, J. Chem. Soc. Chem. Commun., 231 (1995).
6. Nordmark-Werke GmbH, DE2538424 (1975).
7. Seneci et al, J. Chem. Soc. Perkin Trans. I, 2345 (1994).
8. Van Dobeneck et al, Chem. Ber., 105, 3611 (1972).
9. Lee et al, Bioorg. Med. Chem. Lett., 10, 1063 (2000).
10. Kucznierz et al, J. Med. Chem., 41, 4983 (1998).
11. Cesare et al, J. Med. Chem., 35, 4205 (1992).
12. Okada et al, Chem. Pharm. Bull., 41, 132 (1993).
13. Heffner et al, J. Amer. Chem. Soc., 114, 10181 (1992).
14. WO 00/09491, PCT/US/18377 (2000).

NMR data for Example 16: $\delta_H$ (CDCl$_3$) 0.77 (3H, d), 0.88 (3H, d), 1.0–1.8 (15H, m), 2.05–2.35 (5H, m), 3.35 (1H, dd), 4.2–4.4 (4H, m), 4.68 (2H, br s), 5.22 (1H, dd), 5.37 (1H, dd), 5.75 (1H, dd), and 7.08 (1H, s).

NMR data for Example 26: $\delta_H$ (400 MHz; CD$_3$OD) 0.76 (3H, d), 0.93 (3H, d), 1.1–1.2 (1H, br m), 1.16 (3H, s), 1.3–1.7 (6H, m), 1.45 (3H, s), 1.8 (1H, m), 2.1–2.4 (6H, s), 2.6 (1H, m), 3.4 (2H, m) 3.5 (1H, d), 5.15–5.2 (2H, m), 5.3(1H, t) 5.71 (1H, d), 6.34 (1H, dd).

NMR data for Example 43: $\delta_H$ (400 MHz; CD$_3$OD) 0.74 (3H, d), 0.93 (3H, d), 1.10–1.18 (1H, br m), 1.16 (3H, s), 1.33–1.50 (3H, m), 1.45 (3H, s), 1.53–1.72 (3H, m), 1.78–1.86 (1H, m), 2.10–2.38 (5H, m), 3.50 (1H, d), 4.154.20 (2H, m), 4.39–4.46 (2H, m), 5.16 (1H, d), 5.19 (1H, s), 5.29–5.34 (1H, m), 5.71 (1H, d), 6.34 (1H, dd).

NMR data for Example 44: $\delta_H$ (400 MHz; CDCl$_3$) 0.77 (3H, d), 0.88 (3H, d), 1.1 (1H, m), 1.18 (3H, s), 1.45 (3H, s) 1.3–2.4 (15H, m), 3.0–3.25 (4H, m), 3.35 (1H, d), 5.2 (1H, d), 5.2 (1H, m)5.38 (1H, bd), 5.74 (1H, d) and 6.52 (1H, dd). (NH resonances not seen)

NMR data for Example 45: $\delta_H$ (400 MHz; CDCl$_3$) 0.77 (3H, d), 0.88 (3H, d), 1.1 (1H, m), 1.18 (3H, s), 1.45 (3H, s) 1.3–2.4 (15H, m), 2.9–3.1 (4H, m), 3.35 (1H, d), 5.2 (1H, d), 5.3 m)5.37 (1H, d), 5.74 (1H, d), 6.52 (1H, dd) 7.4 (1H, b).

NMR data for Example 63: $\delta_H$ (400 MHz; CDCl$_3$) 0.76 (3H, d), 0.88 (3H, d), 1.1 (1H, m), 1.18 (3H, s), 1.45 (3H, s) 1.3–2.4 (16H, m), 2.3 (6H, s) 3.35 (1H, d) 3.9 (1H, m), 4.05 (1H, m), 4.25 (1H, m), 5.22 (1H, d), 5.36 (1H, 4)), 5.74 (1H, d), 6.52 (1H, dd) 7.1 (1H, b).

General Procedure B, for the Preparation of Mutilin 14-[N-(alkoxycarbonyl)]carbamates (a) 11-Trifluoroacetylmutilin 14-chloroformate To 11-trifluoroacetylmutilin (WO 97/25309) (4.16 g, 10 mmol) in dry THF (30 ml) at 0° C. under argon was added pyridine (0.808 ml, 10 mmol) and triphosgene (1.09 g, 3.67 mmol, portionwise). After stirring for 10 min at 0° C., hexane (50 ml) was added and the mixture washed with water and brine, and dried. After evaporation the chloroformate was obtained as a white solid (4.3 g, 90%).

(b)) Mutilin 14-[N-(alkoxycarbonyl)]carbamates 11-Trifluoroacetylmutilin 14-chloroformate (0.191 g, 0.4 mmol) was dissolved in dry dichloromethane (2.5 ml) and added to silver cyanate (0.09 g, 0.6 mmol). To this stirred suspension was added pyridine (0.008 g, 0.1 mmol) in dry dichloromethane (0.1 ml). After 1.5 min the appropriate alcohol (0.4–2 mmol) in dry dichloromethane or DMF was added. The mixture was stirred for 3.5 h, then treated with water (0.1 ml), and ethyl acetate added (10 ml). This mixture was then filtered through hydromatrix gel and kieselguhr. After evaporation the residue was dissolved in ethanol (8 ml) and saturated aqueous sodium hydrogen carbonate (8 ml) added. The mixture was stirred for 6 h, then filtered and the filtrate extracted with ethyl acetate. The filtered solid was slurried in the aqueous phase and extracted with ethyl acetate. The combined organic extracts were washed with brine, dried and evaporated. The residue was purified by column chromatography on silica gel, eluting with 20–100% ethyl acetate in petroleum ether then 0–10% methanol in dichloromethane, to give the required product.

Examples 69–90

Examples 69–90 were prepared by general procedure B. In the case of Example 77 the crude material (after having been filtered through hydromatrix gel and kieselguhr and then evaporated) was treated with trifluoroacetic acid (1 ml) for 1 h then concentrated in vacuo. After evaporation the residue was taken up in ethanol (10 ml) and saturated sodium hydrogen carbonate (10 ml). The mixture was stirred for 2.5 h, then worked up as in the general procedure.

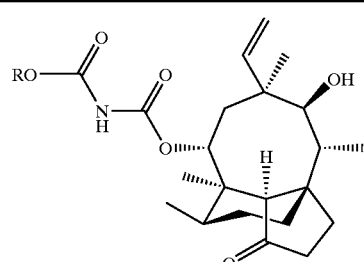

| Example | R | Alcohol | MW | Yield | LC/MS |
|---|---|---|---|---|---|
| 69 | 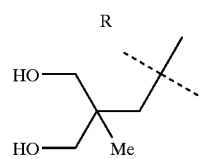 | C | 509 | 15% | 508 (ES−) [M − H]⁻ 100% |
| 70 | 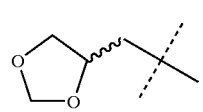 | C^ | 493 | 27% | 492 (APCI−) [M − H]⁻ 100% |
| 71 | 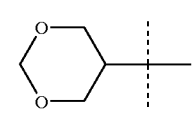 | C^ | 493 | 10% | 492 (APCI−) [M − H]⁻ 100% |
| 72 | 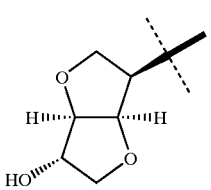 | C | 535 | 9% | 534 (APCI−) [M − H]⁻ 100% |
| 73 | 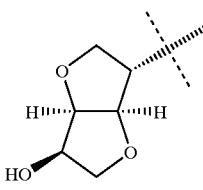 | C, $ | 535 | 5% | 558 (ES+) [MNa]⁺ 50% |
| 74 | 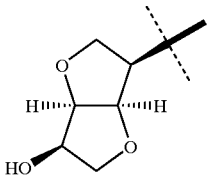 | C, $ | 535 | 50% | 558 (ES+) [MNa]⁺ 100% |
| 75 | 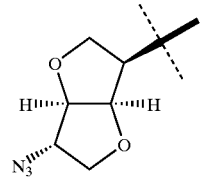 | Int. 19 | 560 | 81% | 559 (APCI−) [M − H]⁻ 100% |

-continued
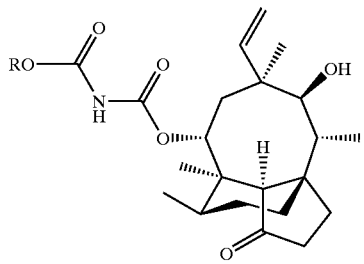
| Example | R | Alcohol | MW | Yield | LC/MS |
|---|---|---|---|---|---|
| 76 | 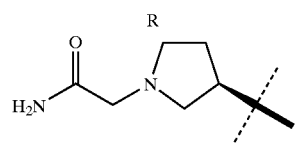 | Ref 15 | 533 | 27% | 534 (ES+) [MH]+ 100% |
| 77 | 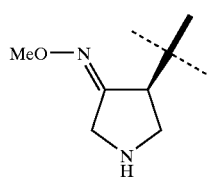 | Int. 20 | 519 | 31% | 520 (ES+) [MH]+ 100% |
| 78 | 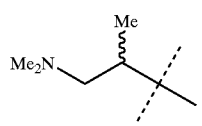 | C | 492 | 43% | 493 (ES+) [MH]+ 100% |
| 79 | 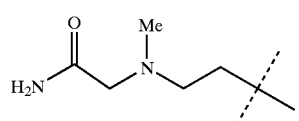 | Ref 15 | 521 | 25% | 522 (ES+) [MH]+ 100% |
| 80 | 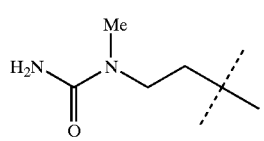 | Ref 16 | 507 | 42% | 530 (ES+) [MNa]+ 100% |
| 81 | 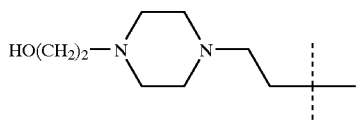 | C | 563 | 13% | 562 (ES−) [M − H]− 100% |
| 82 | 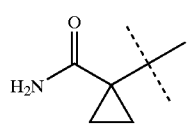 | Int. 21 | 490 | 43% | 513 (ES+) [MNa]+ 100% |
| 83 | 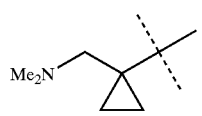 | Int. 22 | 504 | 16% | 505 (ES+) [MH]+ 100% |
| 84 | 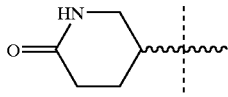 | C | 504 | 34% | 503 (ES−) [M − H]− 100% |
| 85 | 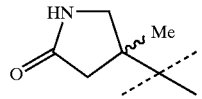 | C | 504 | 28% | 503 (APCI−) [M − H]− 100% |

-continued

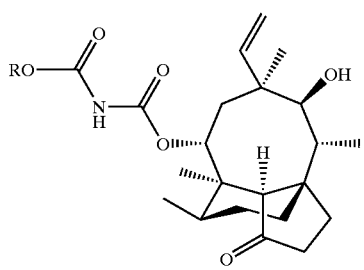

| Example | R | Alcohol | MW | Yield | LC/MS |
|---|---|---|---|---|---|
| 86 | (3,3-dimethyl-2-oxopyrrolidin-substituent with Me, Me) | Ref 17 | 518 | 59% | 517 (ES−) [M − H]⁻ 100% |
| 87 | (succinimidyl-CMe₂-) | Ref 18 | 518 | 10% | 517 (APCI−) [M − H]⁻ 100% |
| 88 | (succinimidyl-CH₂-CMe₂-) | C | 532 | 33% | 531 (APCI−) [M − H]⁻ 100% |
| 89 | Me-S-CH₂-CMe₂- | Ref 19 | 467 | 8.5% | 466 (APCI−) [M − H]⁻ 100% |
| 90 | (1,1-dioxothietan-3-yl with Me) | Ref 20 | 511 | 6% | 510 (ES−) [M − H]⁻ 100% |

C commercially available alcohol;

^ both examples isolated from reaction with the commercially available mixture of 1,3-dioxan-5-ol and 1,3-dioxolane-4-methanol;

$ both isomers obtained from the reaction with the same alcohol.

References:

15. Kamiya et al, EP 264091 (1988).

16. Miyahara et al, Chem. Pharm. Bull., 33, 497 (1985)

17. Kopelevich et al, Chem. Nat. Compd. (Engl. Transl.), 18, 215 (1982).

18. Mahfouz et al, Eur. J. Med. Chem. Chim. Ther., 34, 551 (1999).

19. Jones et al, Synth. Commun., 16, 1607 (1986).

20. Dittmer and Christy, J. Org. Chem., 26, 1324 (1961).

NMR data for Example 83: $\delta_H$ (400 MHz; CD$_3$OD) 0.74–0.82 (5H, m), 0.90–0.98 (5H, m), 1.10–1.18 (1H, br m), 1.16 (3H, s), 1.28–1.47 (3H, m), 1.44 (3H, s) 1.55–1.72 (3H, m) 1.78–1.84 (1H, m), 2.10–2.35 (5H, m), 2.33 (6H, s), 2.68–78 (2H, m), 3.48 (1H, d), 5.14–5.21 (2H, m), 5.70 (1H, d), 6.35 (1H, dd).

General Procedure C, for the Preparation of Mutilin 14-[N-(alkoxycarbonyl)]carbamate Amide Derivatives To the acid Intermediate 23 or Intermediate 24 (0.20 mmol) dissolved in dry DMF (1 ml) was added 1-hydroxy-7-azabenzotriazole (0.030 g, 0.22 mmol) in DMF (1 ml), followed by the amine (0.22 mmol; in the case of Example 97, 0.44 mmol), [and diethylaminomethyl-polystyrene (0.40 mmol) in the case of amine hydrochlorides] and, after 30min, 1-[3-(dimethylamino)propyl]-3-ethylcarbodiimide hydrochloride (0.042 g, 0.22 mmol). The mixture was stirred under argon for 24 h, water (1 ml) and saturated sodium hydrogen carbonate solution (1 ml) were added, and the mixture filtered through hydromatrix gel and washed through with ethyl acetate. The filtrate was concentrated in vacuo then purified by flash column chromatography on silica gel, eluting with 20–100% ethyl acetate in petroleum ether then 0–20% methanol in dichloromethane to give the title compounds.

Examples 91–99

Examples 91–99 were prepared by general procedure C.

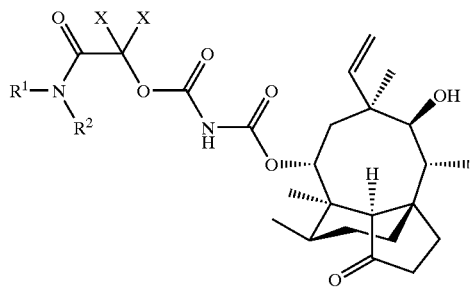

| Example | Acid | R$^1$R$^2$N— | X | MW | Yield | LC/MS (ES+) |
|---|---|---|---|---|---|---|
| 91 | Int 23 | MeNH | H | 478 | 81% | 501 [MNa]$^+$, 100% |
| 92 | Int. 23 | Me$_2$N | H | 492 | 78% | 515 [MNa]$^+$, 100% |
| 93 | Int. 23 | MeO(CH$_2$)$_2$NH | H | 522 | 72% | 545 [MNa]$^+$, 100% |
| 94 | Int. 23 | NCCH$_2$NH | H | 503 | 68% | 526 [MNa]$^+$, 100% |
| 95 | Int. 23 | MeONH | H | 494 | 72% | 517 [MNa]$^+$, 100% |
| 96 | Int 23 | morpholinyl | H | 534 | 85% | 557 [MNa]$^+$, 100% |
| 97 | Int. 23 | piperazinyl | H | 533 | 45% | 534, [MH]$^+$ 100% |
| 98 | Int. 23 | (pyridin-3-ylmethyl)NH | H | 555 | 78% | 556 [MH]$^+$, 100% |
| 99 | Int. 24 | MeNH | Me | 506 | 61% | 529 [MNa]$^+$, 100% |

All amines were commercially available; that for Example 95 was used as the hydrochloride salt.

General Procedure D, for the Preparation of Mutilin (2S)-hydroxy-14-[N-(alkoxycarbonyl)]carbamates (a) (2S)-2-Dichloroacetoxy-11-O-trifluoroacetyl-mutilin 14-chloroformate The title as prepared as in the method of Example 12 of patent PCT/EP96/05874 from (2)-2-dichloroacetoxy-11-O-trifluroacetyl-mutilin.

(b) Mutilin (2S)-hydroxy-14-[N-(alkoxycarbonyl)] carbamates (2S)-2-Dichloroacetoxy-11-O-trifluoroacetyl-mut 14-chloroformate (0.242 g, 0.40 mmol) was dissolved in dry dichloromethane (2.5 ml) and added to silver cyanate (0.09 g, 0.60 mmol). To this stirred suspension was added pyridine (0.008 g, 0.10 mmol) in dry dichloromethane (0.1 ml). After 1.5 min the appropriate alcohol in dry dichloromethane or DMF was added. The mixture was stirred for 3.5 h, then treated with water (0.1 ml), and ethyl acetate added (10 ml). This mixture was then filtered through hydromatrix gel and kieselguhr. After evaporation the residue was dissolved in ethanol (8 ml) and saturated aqueous sodium hydrogen carbonate (8 ml) added. The mixture was stirred for 6 h, then filtered and the filtrate extracted with ethyl acetate. The filtered solid was slurried in the aqueous phase and extracted with ethyl acetate. The combined organic extracts were washed with brine, dried and evaporated. The residue was purified by flash column chromatography on silica gel, eluting with 20–100% ethyl acetate in petroleum ether then 0–10% methanol in dichloromethane, or by reverse phase HPLC eluting with acetonitrile in water (with TFA 0.1%) to give the title compounds.

Examples 100 and 101

Examples 100 and 101 were prepared by general procedure D.

| Example | R | Alcohol | MW | Yield | LC/MS |
|---|---|---|---|---|---|
| 100 | ![HO-CH2-C(CH3)2-] | C | 467 | 74% | 490 (ES+) [MNa]+ 100% |
| 101 | ![HO-CH2-pyridine-CH2-] TFA salt | C | 544 | 33% | 545 (ES+) [MH]+ 100% |

General Procedure E, for Reduction of the 19,20 Double Bond

To the starting material (0.05 mmol) in THF (2 ml) under argon was added 10% palladium on carbon (20 mg) and the mixture treated with hydrogen gas at 1 atm with shaking for 2 h. The reaction mixture was filtered through kieselguhr, and the filter pad washed well with THF. The combined filtrates were evaporated to dryness, in general no purification was necessary.

Examples 102–105

Examples 102–105 were prepared by general procedure E.

| Example | Reactant | R¹ | R² | MW | Yield | LC/MS |
|---|---|---|---|---|---|---|
| 102 | Ex. 3 | HO-CH₂-C(CH₃)₂- | OH | 469 | 90% | 468 (APCI−) [M − H]⁻ 100% |
| 103 | Ex. 7 | H₂N-CH₂-C(CH₃)₂- | H | 466 | 95% | 465 (APCI−) [M − H]⁻ 100% |
| 104 | Ex. 27 | (5-oxopyrrolidin-2-yl)methyl-C(CH₃)₂- | H | 506 | 99% | 505 (APCI−) [M − H]⁻ 100% |
| 105 | Ex. 34 | 3-methylpyrrolidin-3-yl | H | 478 | 85% | 479 (APCI+) [MH]⁺ 100% |

Example 106

Mutilin 14-[N-(1-methanesulfonylpyrrolidin-3-(S)-yloxycarbonyl)]carbamate

To the compound of Example 45 (0.049 g, 0.1 mmol) dissolved in dry dichloromethane (2 ml) under argon was added pyridine (0.012 ml) and a solution of methanesulfonyl chloride (0.0135 g, 0.12 mmol) in dry dichloromethane (1 ml). The reaction was stirred at 20° C. for 20 h, then ethyl acetate (10 ml) and 1 M hydrochloric acid (1 ml) were added. The phases were separated, and the aqueous layer extracted with further ethyl acetate (10 ml). The combined organic layers were dried by passage through a hydromatrix gel column, evaporated to dryness and purified by chromatography on a Biotage Quad 3 eluting with 0–13% methanol in dichloromethane. The product containing fractions were combined and evaporated to dryness to give the title product, as a white foam (0.037 g, 66%).

Related derivatives were prepared by the same method using the amine Example 45 or 57 and using methanesulfonyl chloride/pyridine, sulfamoyl chloride/triethylamine or 2 equivalents of trimethylsilyl isocyanate.

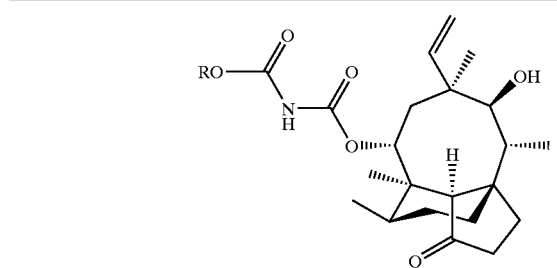

| Example | Amine | R | MW | Yield | LC/MS |
|---|---|---|---|---|---|
| 106 | Ex. 45 | Me-SO₂-N(pyrrolidin-3-yl) | 554 | 66% | 553 (ES−) [M − H]⁻ 100% |
| 107 | Ex. 57 | Me-SO₂-N(morpholin-2-yl) | 584 | 72% | 583 (ES−) [M − H]⁻ 100% |

-continued

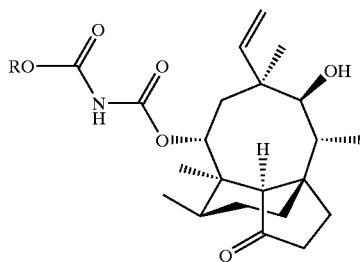

| Example | Amine | R | MW | Yield | LC/MS |
|---|---|---|---|---|---|
| 108 | Ex. 57 | H₂N-S(O₂)-N(morpholine-CH2)- | 585 | 24% | 584 (ES−) [M −H]⁻ 100% |
| 109 | Ex. 57 | H₂N-C(O)-N(morpholine-CH2)- | 549 | 23% | 548 (ES−) [M − H]⁻ 100% |
| 110 | Ex. 45 | H₂N-C(O)-N(pyrrolidine)- | 519 | 44% | 518 (ES−) [M − H]⁻ 100% |

Example 111

Mutilin 14-[N-(1-glycylpyrrolidin-3(R)-yloxycarbonyl)]carbamate

To the compound of Example 44 (0.05 g, 0.105 mmol) dissolved in dry DMF (0.5 ml) under argon was added Boc-glycine (0.019 g), HOAT (0.014 g) and EDAC (0.021 g). The reaction was stirred at 20° C. for 20 h, and concentrated by evaporation under reduced pressure. The residue was taken up in ethyl acetate and water (10 ml, 1 ml), the organic phase washed with saturated aqueous sodium hydrogen carbonate, and the aqueous phases re-extracted with ethyl actate. The combined organic phases were dried and evaporated to low volume under reduced pressure. The residue was treated with trifluoroacetic acid (4 ml) at 20° C. for 15 min, then evaporated to dryness under reduced pressure and purified by chromatography on silica gel eluting with 0–10% 2M methanolic ammonia in dichloromethane to give the title product as a white foam (0.041 g, 77%).

Further products were made from the products of Examples 44, 45 and 57 using the same procedure but substituting the appropriate carboxylic acid for Boc-glycine and omitting the TFA treatment.

| Example | Amine | R | MW | Yield | LC/MS |
|---|---|---|---|---|---|
| 111 | Ex. 44 | H₂N-CH2-C(O)-N(pyrrolidine)- | 533 | 77% | 532 (ES−) [M − H]⁻ 100% |
| 112 | Ex. 45 | H₂N-C(O)-C(O)-N(pyrrolidine)- | 547 | 80% | 546 (ES−) [M − H]⁻ 100% |

-continued

| Example | Amine | R | MW | Yield | LC/MS |
|---|---|---|---|---|---|
| 113 | Ex. 44 | 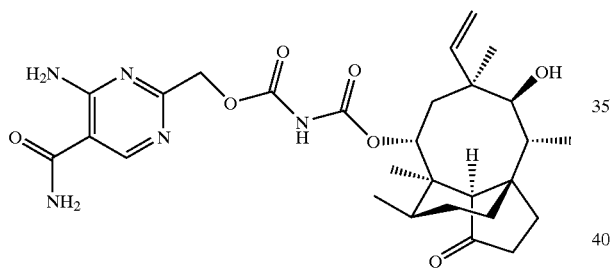 | 570 | 60% | 593 (APCI+) [MNa]+ 15% |
| 114 | Ex. 57 | | 577 | 65% | 576 (ES−) [M − H]− 100% |
| 115 | Ex. 57 | | 626 | 46% | 625 (ES−) [M − H]− 100% |

Example 116
Mutilin 14-[N-(4-amino-5-carboxamidopyrimidin-2-ylmethoxycarbonyl)]carbamate

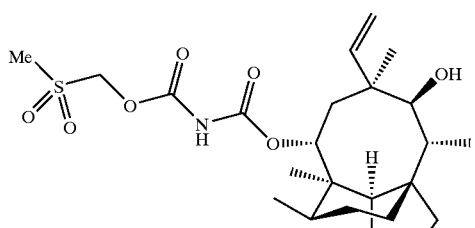

The compound of Example 37 (0.1 g, 0.185 mmol) was treated with conc. HCl (20 ml) for 4 h. The reaction was evaporated to dryness under reduced pressure and the residue purified by chromatography on silica gel eluting with 2–6% 2M methanolic ammonia in dichloromethane to give recovered starting material, (0.04 g) and the title product as a pale yellow foam (0.022 g, 35% based on recovered starting material), LC/MS (APCI+) 558 [MH]+ 100%.

Example 117
Mutilin 14-[N-(methylsulfonylmethoxycarbonyl)] carbamate

To the compound of Example 89 (0.052 g, 0.11 mmol) in dichloromethane (5 ml) at 0° C. was added meta-chloroperbenzoic acid (MCPBA, 0.035 g) and the mixture stirred at 0° C. for 30 min and a further 30 min at 20° C. A further 0.005 g MCPBA was added and the reaction stirred at 20° C. for 2 h. The reaction mix was washed with saturated aqueous sodium hydrogen carbonate (2 ml), dried and purified by chromatography on silica gel eluting with 10–50% ethyl acetate in dichloromethane, to give the title material as a colourless foam (0.032 g, 58%), LC/MS (APCI+) 517 [M.NH$_4$]+ 100%.

Example 118
Mutilin 14-[-(cis-4-carbamoyloxytetrahydrofuran-3-yloxycarbonyl)]carbamate

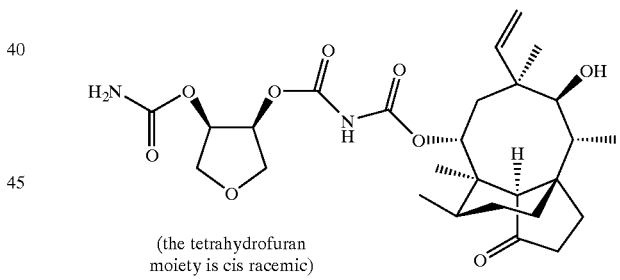

(the tetrahydrofuran moiety is cis racemic)

11-Trifluoroacetylmutilin 14-chloroformate (0.275 g, 0.57 mmol) was disolved in dry dichloromethane (5 ml) and added to silver cyanate (0.13 g). To this stirred suspension was added pyridine (0.015 g). After 1.5 min 1,4-anhydroerythritol (0.14 ml) was added. The mixture was stirred for 3.5 h then treated with water (0.1 ml), ethyl acetate (10 ml) was added, and the mixture filtered through hydromatrix gel and kieselguhr. After evaporation the residue was purified by column chromatography on silica gel, eluting with 40–70% ethyl acetate in petroleum ether, to give 11-trifluoroacetylmutilin-14-[N-(cis-4-hydroxytetrahydrofuran-3-yloxycarbonyl)]carbamate, (0.18 g, 57%). This material (0.069 g) in dry THF (2 ml) was treated with carbonyl diimidazole (0.13 g) at 20° C. for 1.5 h, then aqueous ammonia (20 M, 0.1 ml) was added. After stirring at 20° C. for 2 h, the solvent was evaporated and the residue triturated with dichloromethane/methanol (9:1, 2 ml). The soluble material was purified by chromatography on silica gel eluting with 30–100% ethyl acetate in hexane to give the title material (0.02 g, 30%), LC/MS (ES−) 492 [M-CONH2]⁻ 100%, 535 [M-H]⁻ 30%.

Example 119

Mutilin 14-[N-((2-amino-3-carbamoylpyrazin-5-yl)methyloxycarbonyl)]carbamate

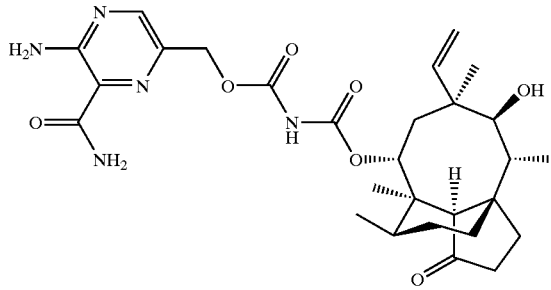

(a) 5-Acetoxymethyl-2-bis(tert-butoxycarbonyl)amino-3-cyanopyrazine 5-Acetoxymethyl-2-amino-3-cyanopyrazine (0.46 g, 2.4 mmol) was suspended in dichloromethane (18 ml), then triethylamine (0.81 ml, 5.8 mmol) added followed by di-t-butyldicarbonate (1.2 g, 5.5 mmol) and DMAP (few mgs). The mixture was stirred for 1 h, then washed with water and brine, dried and evaporated to give the crude title compound as a pale brown oily solid (1.05 g, q); NMR (CDCl₃) 1.47 (18H, s), 2.20 (3H, s), 5.32 (2 h, s), and 8.73 (1H, s). This material was used without further purification.

(b) 2-Bis(tert-butoxycarbonyl)amino-3-cyano-5-(hydroxymethyl)pyrazine The crude product from (a) was dissolved in dioxane (10 ml) and water (2 ml) then sodium hydroxide solution (2M, 1.3 ml, 2.6 mmol) added. The mixture was stirred for 5 h, diluted with ethyl acetate, washed with dilute sodium chloride solution then brine, dried and evaporated to give the crude product as a brown gum (0.95 g). This material was chromatographed, eluting with 0–35% ethyl acetate in petroleum ether, to give the required product contaminated with an impurity (5-acetoxymethyl-2-tert-butoxycarbonylamino-3-cyanopyrazine) (0.172 g).

(c) Mutilin 14-[N-((2-amino-3-carbamoylpyrazin-5-yl)methyloxycarbonyl)]carbamate Impure 2-bis(tert-butoxycarbonyl)amino-3-cyano-5-(hydroxymethyl)pyrazine (0.16 g, ~0.22 mmol) was then reacted as in general method A. During the treatment with concentrated hydrochloric acid the cyano group was hydrolysed to the primary amide and the tert-butoxycarbonyl groups removed to give the title compound as a pale yellow foam (0.026 g, 21%); LC/MS (ES+) 580 (MNa+), 100%.

Example 120

Mutilin 14-[N-(2-(4-formylpiperazin-1-yl)ethyloxycarbonyl)]carbamate

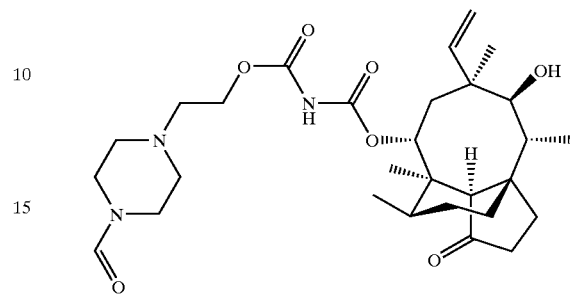

To the compound of Example 65 (0.13 g, 0.25 mmol) dissolved in dry dimethylformamide (2 ml) under argon was added formic acid (0.044 ml, 1.2 mmol), 1-ethyl-3-(3-dimethylaminopropyl)carbodiimide hydrochloride (0.114 g, 0.6 mmol) and 1-hydroxy-7-azabenzotriazole (0.041 g, 0.3 mmol). The mixture was stirred for 6 h then diluted with ethyl acetate and aqeous sodium hydrogen carbonate (1 ml), passed through hydromatrix gel, and evaporated. The crude product was purified by chromatography to give the title compound as a white foam (0.104 g, 63%); LC/MS (ES−) 546 [M-H]⁻, 100%.

Example 121

Mutilin 14-[N-(2-(4-sulphamoylpiperazin-1-yl)ethyloxycarbonyl)]carbamate

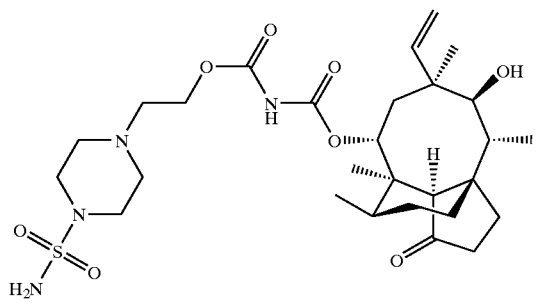

To the compound of Example 65 (0.104 g, 0.2 mmol) dissolved in dry dichloromethane (2 ml) under argon was added triethylamine (0.031 ml, 0.22 mmol) followed by a solution of sulphamoyl chloride (0.024 g, 0.21 mmol) in dry dichloromethane (1 ml). Stirred for 2 h then further portions of reagents added. After a further 2 h the mixture was chromatographed to give the title compound as an off-white foam (0.030 g, 25%); LC/MS (ES−) 597 [M-H]⁻, 100%.

Example 122

Mutilin 14-[N-(((3R,3aR,6S,6aR)-6-amino-hexahydrofuro[3,2-b]furan-3-yl)oxycarbonyl)]carbamate

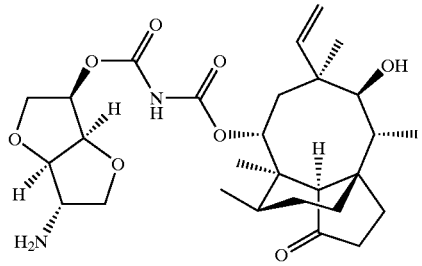

Mutilin 14-[N-(((3R,3aR,6S,6aR)-6-azido-hexahydrofuro[3,2-b]furan-3-yl)oxycarbonyl)]carbamate (0.56 g, 1 mmol) was dissolved in tetrahydrofuran (14 ml) then triphenylphosphine (0.524 g, 2 mmol) and water (0.3 ml) added. The mixture was stirred for 43 h then evaporated and chromatographed to give the title compound as a white foam (0.294 g, 55%); LC/MS (ES−) 533 [M−H]−, 100%.

Example 123

Mutilin 14-[N-(1-cyanomethylpyrrolidin-3-(R)-yloxycarbonyl)]carbamate

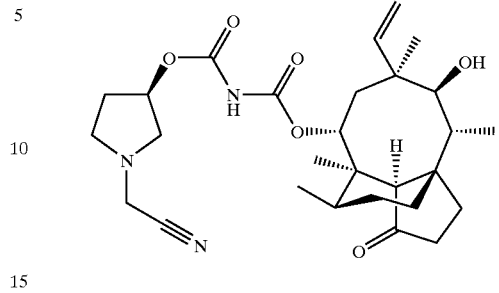

To a solution of the compound of Example 44 (95 mg, 0.2 mmol) in dichloromethane (1 ml) was added bromoacetonitrile (18 ul, 0.25 mmol) followed by triethylamine (35 ul, 0.25 mmol) and the solution was stirred at RT for 3 h. The solution was partitioned between saturated aqueous sodium hydrogen carbonate and dichloromethane, and the organic layer was dried (MgSO$_4$) and evaporated. The residue was purified by column chromatography on silica gel eluting with 0.5% '2 M ammonia in methanol' in ethyl acetate. The product was triturated with ether-hexane to afford the title compound as a white solid (78 mg, 76%); LC/MS (APCI+) 538 [MH]+, 100%.

Examples 124 and 125

Examples 124 and 125 were prepared by general procedure A. The aqueous work-up was omitted and the residue was purified by column chromatography on silica gel eluting with 0–15% 2M methanolic ammonia in dichloromethane.

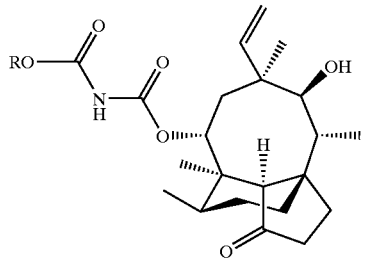

| Example | R | Alcohol | MW | Yield | LC/MS |
|---|---|---|---|---|---|
| 124 | H$_2$N— (tetrahydrofuran-amine structure) | Int 25 | 492 | 12% | 491 (APCI−) [M − H]− 100% |
| 125 | H$_2$N— (cyclopentane structure) cis racemic | Ref 21, # | 490 | 59% | 491 (ES+) [M + H]+ 100% |

Starting alcohol is N-Boc derivative;

Reference 21: Hodgson et al, *Tetrahedron Lett.;* 39, 3357 (1998).

Example 126

Mutilin 14[N-(5-(S)-cyanopyrrolidin-3-(R)-yloxycarbonyl)]carbamate

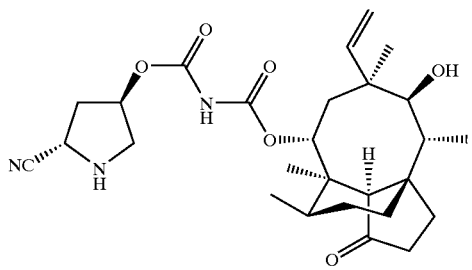

a) N-o-Nitrophenylsulphenyl trans-4-hydroxy-L-proline
To trans-4-hydroxy-L-proline (6.0 g, 45.8 mmol) in dioxan (60 ml) and 2 M sodium hydroxide (23 ml) was added portionwise o-nitrobenzenenesulfenyl chloride (9.5 g, 50 mmol) with simultaneous addition of 2 M sodium hydroxide (23 ml). The resulting orange reaction mixture was diluted with water (200 ml) and washed with diethyl ether. The aqueous solution was cooled in ice, acidified to pH 2.5 with c HCl and extracted with ethyl acetate. The organic layer was washed with brine, dried ($MgSO_4$) and evaporated to a gum. Diethyl ether (100 ml) was added and the mixture sonicated to give an orange solid which was removed by filtration and washed with diethyl ether to give the title material, (9.4 g, 72%); NMR (CD3OD) 2.3 (2H, m), 3.1 (1H, bs), 3.7 (1H, bs), 4.16 (1H, t), 4.5 (1H, bs), 7.32 (1H, dt), 7.7 (1H, dt),8.25 (1H, bs), 8.27(1H, d).

b) N-o-Nitrophenylsulphenyl trans-4-hydroxy-L-prolinamide To N-o-nitrophenylsulphenyl trans-4-hydroxy-L-proline (5.68 g, 20 mmol) in DMF was added N-hydroxysuccinimide (2.5 g) and 1-ethyl-3-(3-dimethylaminopropyl)carbodiimide hydrochloride (3.9 g). After 75 min, ammonium hydrogen carbonate (2 g) and triethylamine (2.8 ml) was added and the mixture stirred for 2.5 h. Water (20 ml) was added and the mixture evaporated to low volume under reduced pressure. To the residue was added 5% methanol in dichloromethane and the insoluble solid removed by filtration. The filtrate was purified by chromatography on silica gel eluting with 0–12% (2 M methanolic ammonia) in dichloromethane to give the title compound, (5.1 g) which contained a trace of N-hydroxysuccinamide; NMR ($CD_3OD$) 2.2 (2H, m), 3.2. (1H, bd), 3.8 (1H, bd), 4.15 (1H, t), 4.5 (1H, bm), 7.3 (1H, dt), 7.7 (1H, dt),8.25 (1H, bd), 8.25 (1H, d).

c) 2-(S)-Cyano-4-(R)-hydroxy-1-o-nitrophenylsulphenylpyrrolidine To N-o-nitrophenylsulphenyl trans-4-hydroxy-L-prolinamide (0.566 g, 2 mmol) in THF (5 ml) at 0° C. under argon was added triethylamine (1.7 ml) and trifluoroacetic acid anhydride (TFAA; 0.85 ml). After 45 min further portions of added triethylamine (1.7 ml) and TFAA (0.85 ml) were added. After a further 45 min water (20 ml) was added, the mixture extracted with diethyl ether and the organic solution dried and evaporated. The residue was purified by chromatography on silica to give the title material as a pale yellow gum, (0.41 g, 77%); NMR (CDCl₃) 1.9 (1H, bs), 2.5 (2H, bm), 3.2 (1H, bm), 3.8 (1H, bs), 4.5 (1H, t), 4.65 (1H, bs), 7.35 (1H, dt), 7.65 (1H, dt), 8.0 (1H, bm), 8.3 (1H, dd).

d) Mutilin 14-[N-(5-(S)-cyanopyrrolidin-3-(R)-yloycarbonyl)]carbamate 2-(S)-Cyano-4-(R)-hydroxy-1-o-nitrophenylsulphenylpyrrolidine (0.133 g, 0.5 mmol) was subjected to general procedure B, to give mutilin 14-[N-(2-(S)-cyano-1-o-nitrophenylsulphenylpyrrolidin-4-(R)-yloxycarbonyl)]carbamate, (0.141 g). This material was dissolved in dichloromethane (5 ml) and treated with 1 M HCl in diethyl ether (1.5 ml)

After 10 min, the precipitated material was collected and purified by chromatography on silica gel eluting with 0–10% (2M methanolic ammonia) in dichloromethane to give the title compound as a pale yellow foam, (50 mg, 20%); LC/MS (ES–) 500 (M–H⁻), 30%.

Example 127

19,20-Dihydromutilin 14-[N-(trans-3-aminocyclopentyloxycarbonyl)]carbamate

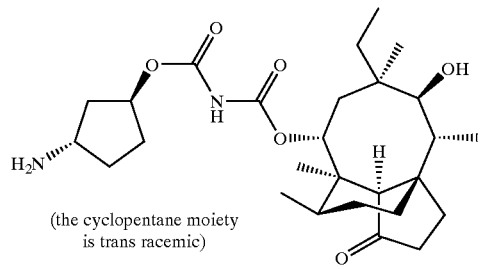

(the cyclopentane moiety is trans racemic)

trans-3-Benzyloxycarbonylaminocyclopenanol (Gregson et al, WO 9417090, 1994) was subjected to general procedure B on a 0.226 mmol scale, to give mutilin 14-[N-(trans-3-benzyloxycarbonylaminocyclopentyloxycarbonyl)] carbamate as a colourless gum (0.07 g, 49%); NMR (CDCl₃) 0.77 (3H, d), 0.87 (3H, d), 1.1–1.9 (19H, m), 2.0–2.4 (7H, m), 3.5 (1H, dd), 4.18 (1H, m), 4.7 (1H, bs). 5.1 (2H, bs), 5.2 (2H, m), 5.37 (1H, d), 5.75 (1H, d), 6.52 (1H, d), 6.1 (1H, bd), 7.3 (5H, bs). To this material in THF (7 ml) under argon was added 10% palladium on carbon (50 mg) and the mixture treated with hydrogen gas at 1 atm with stirring for 2 h. The reaction mixture was filtered through kieselguhr, and the filter pad washed well with THF. The combined filtrates were evaporated to dryness and purified by column chromatography on silica gel eluting with 0–10% 2 M methanolic ammonia in dichloromethane to give the title compound as a colourless foam, (0.037 g, 67%) LC/MS (ES–) 491 (M–H⁻), 100%.

Example 128

Mutilin 14-[N-(1-carbamoylmethylazetidin-3-yloxycarbonyl)]-carbamate

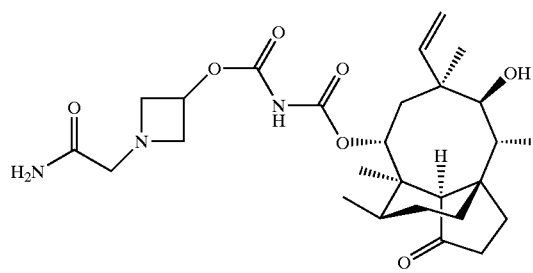

To the compound of Example 43 (0.075 g, 0.15 mmol) and bromoacetamide (0.025 g, 0.18 mmol) dissolved in dry dichloromethane (2 ml) under argon was added triethylamine (0.052 ml, 0.37 mmol). The reaction was stirred for 2.5 h. Purification by flash chromatography, eluting with 0–7% 2 M ammonia in methanol in dichloromethane, gave the required product contaminated with triethylamine hydrochloride. This material was further purified by the use of a SCX cartridge. Washing with methanol then eluting with 0.4–0.8 M ammonia in methanol gave the title compound as a white foam (0.070 g, 91%); LC/MS (ES+) 520 (MH$^+$), 100%.

Example 129

Mutilin 14-[N-(1-cyanomethylazetidin-3-yloxycarbonyl)]-carbamate

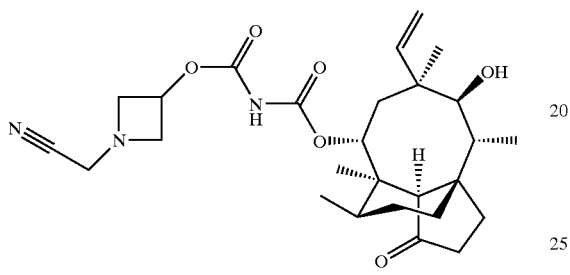

To the compound of Example 43 (0.075 g, 0.15 mmol) and bromoacetonitrile (0.022 g, 0.18 mmol) dissolved in dry dichloromethane (2 ml) under argon was added triethylamine (0.052 ml, 0.37 mmol). After stirring for 3.5 h further portions of bromoacetonitrile and triethylamine were added, and the mixture stirred for another 1 h. The mixture was purified by flash chromatography, eluting with 0–4% 2M ammonia in methanol in dichloromethane, to give the title compound as a white foam (0.063 g, 83%); LC/MS (ES+) 524 (MNa$^+$), 100%.

Example 130

Mutilin 14-[N-(1-aminoazetidin-3-yloxycarbonyl)]-carbamate

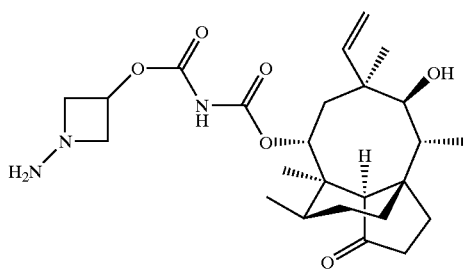

To the compound of Example 43 (0.499 g, 1 mmol) dissolved in dry dichloromethane (20 ml) was added diisopropylethylamine (0.191 ml, 1.1 mmol). The solution was cooled in an ice bath then N-tert-butoxycarbonyl-3-(4-cyanophenyl)oxaziridine (0.271 g, 1.1 mmol) in dry dichloromethane (5 ml) added dropwise. The mixture was stirred for 1.5 h cold and 0.5 h at RT. The volume of the solution was reduced and it was then purified by flash chromatography. Elution with 20–50% ethyl acetate in petroleum ether gave the impure N-tert-butoxycarbonyl protected compound (0.446 g). This material was dissolved in trifluoroacetic acid (5 ml) and stirred for 0.5 h. Evaporation gave a white foam which was purified by flash chromatography, eluting with 0–6% 2M ammonia in methanol in dichloromethane, to give the impure product. Further flash chromatography, eluting with 4–6% methanol in dichloromethane, gave the pure title compound as a white foam (0.203 g, 43%); LC/MS (ES-) 476 [M-H]$^-$, 100%.

Biological Data

Compounds of the present invention were assessed for anti-bacterial activity in a conventional MIC assay against a range of pathogenic organisms.

Examples 1 to 130 were found to have MICs≦4 ug/ml against *Staphylococcus aureus* Oxford, *Streptococcus pneumoniae* 1629, *Moraxella catarrhalis* 1502, and *Haemophilius influenzae* Q1.

What is claimed is:

1. A compound of formula (IA) or (IB):

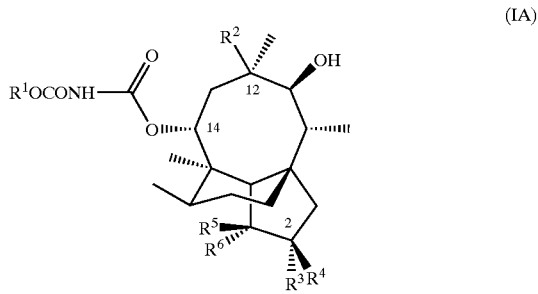

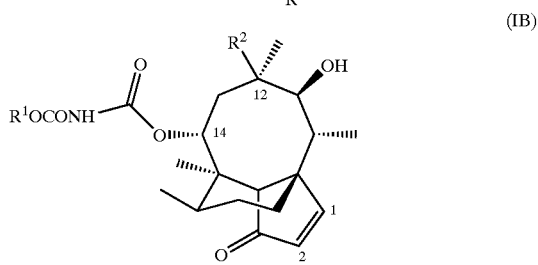

in which:

R$^1$ is optionally substituted C$_{(1-6)}$alkyl or C$_{(3-6)}$cycloalkyl or optionally substituted heterocyclyl;

R$^2$ is vinyl or ethyl;

R$^3$ is H, OH or F, and R$^4$ is H, or R$^3$ is H and R$^4$ is F, and R$^5$ and R$^6$ together form an oxo group; or R$^3$ and R$^4$ is each H, R$^5$ is OH or H and R$^6$ is H, or R$^5$ is H and R$^6$ is OH or H;

or a pharmaceutically acceptable salt thereof.

2. A compound or salt as claimed in claim 1 in which R$^1$ is selected from

C$_{(1-6)}$alkyl or C$_{(3-6)}$cycloalkyl optionally substituted by up to four substituents selected from aryl, heteroaryl, heterocyclyl, (C$_{1-6}$)alkoxy, (C$_{1-6}$)alkylthio, aryl(C$_{1-6}$) alkoxy, aryl(C$_{1-6}$)alkylthio, amino, mono- or di-(C$_{1-6}$) alkylamino, cycloalkyl, cycloalkenyl, carboxy and esters thereof, carbamoyl, ureido, guanidino, (C$_{1-6}$) alkylguanidino, amidino, (C$_{1-6}$)alkylamidino, (C$_{1-6}$) acyloxy, azido, hydroxy, halogen, substituted aryl, substituted heteroaryl, substituted heterocyclyl, substituted amino, carbamoyloxy, ureido substituted by (C$_{1-6}$) alkyl, (C$_{1-6}$)alkylsulphonyl, mono- or di-(C$_{1-6}$) alkylamino(C$_{1-6}$)alkyl, and carbamoyl substituted by 1 or 2 substituents which may be the same or different selected from (C$_{1-6}$)alkyl, (C$_{1-6}$)alkoxy, (C$_{1-6}$)alkoxy (C$_{1-6}$)alkyl, cyano(C$_{1-6}$)alkyl and heteroaryl(C$_{1-6}$) alkyl, or carbamoyl substituted by 2 substituents which together with the nitrogen atom to which they are attached form a heterocyclyl ring; and heterocyclyl optionally substituted by up to three substituents selected from oxo, $(C_{1-6})$alkylimino, halogen, $(C_{1-6})$alkyl, aryl, aryl$(C_{1-6})$alkyl, $(C_{1-6})$alkoxy, $(C_{1-6})$ alkoxy$(C_{1-6})$alkyl, halo$(C_{1-6})$alkyl, aryl$(C_{1-6})$alkoxy, hydroxy, nitro, cyano, azido, amino, mono- and di-N-$(C_{1-6})$alkylamino, acylamino, arylcarbonylamino, acyloxy, carboxy, carboxy salts, carboxy esters, carbamoyl, mono- and di-N-$(C_{1-6})$alkylcarbamoyl, $(C_{1-6})$ alkoxycarbonyl, aryloxycarbonyl, ureido, guanidino, $(C_{1-6})$alkylguanidino, amidino, $(C_{1-6})$ alkylamidino, sulphonylamino, aminosulphonyl, $(C_{1-6})$ alkylthio, $(C_{1-6})$alkylsulphinyl, $(C_{1-6})$alkylsulphonyl, heterocyclyl, heteroaryl, heterocyclyl$(C_{1-6})$alkyl, heteroaryl$(C_{1-6})$alkyl substituted $(C_{1-6})$alkyl, substituted amino, amino$(C_{1-6})$alkyl, amino$(C_{1-6})$ alkylcarbonyl, oxamoyl, carbamoyl$(C_{1-6})$alkyl, cyano $(C_{1-6})$alkyl, acyl, carbamoyloxy, carbamoyloxy$(C_{1-6})$ alkyl and optionally substituted heteroarylcarbonyl, or two adjacent ring carbon atoms are linked by a $(C_{3-5})$ alkylene chain, to form a carbocyclic ring.

3. A compound or salt as claimed in claim 1 in which $R^1$ is $C_{(1-6)}$alkyl optionally substituted by 1, 2 or 3 substituents selected from heteroaryl optionally substituted by 1, 2 or 3 substituents selected from $C_{(1-6)}$alkyl, hydroxy$C_{(1-6)}$alkyl, amino, amino$C_{(1-6)}$alkyl, carbamoyl, cyano and hydroxy, heterocyclyl optionally substituted by 1, 2 or 3 substituents selected from oxo, $C_{(1-6)}$alkyl, hydroxy$C_{(1-6)}$alkyl, aminosulphonyl, carbamoyl and acyl, amino substituted by 1 or 2 substituents which may be the same or different selected from oxamoyl (optionally substituted on N by hydroxy$(C_{1-6})$alkyl), acyl, $(C_{1-6})$ alkylsulphonyl, $(C_{1-6})$alkyl (optionally substituted by, for example, hydroxy), and carbamoyl$(C_1 6)$alkyl, carbamoyloxy, ureido substituted by $C_{(1-6)}$alkyl, $C_{(1-6)}$ alkylsulphonyl, hydroxy, halogen, $C_{(1-6)}$alkylthio, and $R^7R^8NCO$ wherein $R^7$ and $R^8$ which may be the same or different is each selected from hydrogen, $(C_{1-6})$alkyl, $(C_{1-6})$alkoxy, $(C_{1-6})$alkoxy$(C_{1-6})$alkyl, cyano$(C_{1-6})$ alkyl and heteroaryl$(C_{1-6})$alkyl or $R^7$ and $R^8$ together with the nitrogen atom to which they are attached form a heterocyclyl ring.

4. A compound or salt as claimed in claim 3 in which $R^1$ is selected from $C_{(1-6)}$alkyl substituted by carbamoyloxy and $C_{(1-6)}$alkyl substituted by hydroxy and di-N-$C_{(1-6)}$ alkylamino.

5. A compound or salt as claimed in claim 1 in which $R^1$ is $C_{(3-6)}$cycloalkyl substituted by amino, carbamoyl or di-$C_{(1-6)}$ alkylamino$C_{(1-6)}$alkyl.

6. A compound or salt as claimed in claim 5 in which $R^1$ is $C_{(3-6)}$cycloalkyl substituted by di-$C_{(1-6)}$alkylamino$C_{(1-6)}$ alkyl.

7. A compound or salt as claimed in claim 1 in which $R^1$ is a 4- to 6-membered heterocyclyl ring or two fused 5-membered heterocyclyl rings containing 1 or 2 heteroatoms in each ring (for example tetrahydrofuran, 1,3-dioxane, hexahydrofuro[3,2-b]furan, trimethylenesulphide, tetrahydrothiophene, azetidine, pyrrolidine, isoxazolidine or piperidine) optionally substituted by 1, 2 or 3 substituents selected from $C_{(1-6)}$alkyl, hydroxy, hydroxy $C_{(1-6)}$alkyl, $C_{(1-6)}$alkylsulphonyl, $C_{(1-6)}$alkoxy, oxo, oxamoyl, carbamoyl, carbamoyl $C_{(1-6)}$alkyl, carbamoyloxy, carbamoyloxy$C_{(1-6)}$ alkyl, amino$C_{(1-6)}$alkylcarbonyl amino (optionally substituted by oxamoyl), $C_{(1-6)}$alkoxyimino, azido, cyano, cyano $(C_{1-6})$alkyl and heteroarylcarbonyl (optionally substituted by, for example, amino).

8. A compound or salt as claimed in claim 7 in which $R^1$ is a 4- or 5-membered heterocyclyl ring containing one nitrogen atom optionally substituted by oxo.

9. A compound or salt as claimed in claim 1 in which $R^3$ and $R^4$ are both hydrogen, and $R^5$ and $R^6$ together form an oxo group.

10. A compound according to claim 1 selected from:

Mutilin 14-[N-(2-carbamoyloxyethoxycarbonyl)] carbamate;

Mutilin 14-[N-(2-oxopyrrolidin-3-(S)-yloxycarbonyl)] carbamate;

Mutilin 14-[N-(azetidinyloxycarbonyl)]carbamate hydrochloride;

Mutilin 14-[N-(pyrrolidin-3-(R)-yloxycarbonyl)] carbamate;

Mutilin 14-[N-(pyrrolidin-3-(S)-yloxycarbonyl)] carbamate;

Mutilin 14-[N-(3-dimethylamino-2-hydroxyprop-1-yloxycarbonyl)]carbamate; and

Mutilin 14-[N-(1-(dimethylaminomethyl) cyclopropoxycarbonyl)]carbamate;

or a pharmaceutically acceptable salt thereof.

11. A method of preparing a compound of formula (IA) or (IB) which process comprises:

(a) reacting a chloroformate compound of formula (IIA) or (IIB):

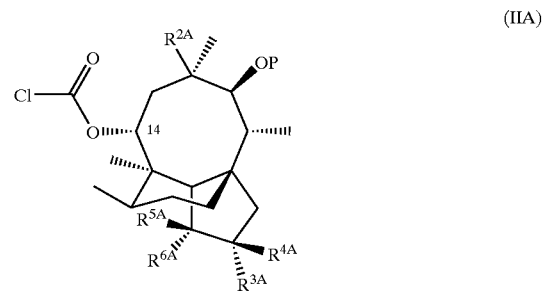

(IIA)

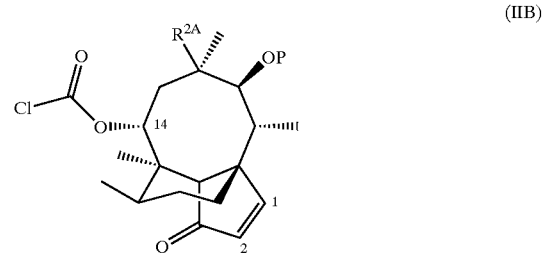

(IIB)

in which:

P is hydrogen or an hydroxy-protecting group;

$R^{2A}$, $R^{3A}$, $R^{4A}$, $R^{5A}$ and $R^{6A}$ are $R^2$, $R^3$, $R^4$, $R^5$ and $R^6$ as defined for formulae (IA) and (IB) or a group convertible to $R^2$, $R^3$, $R^4$, $R^5$ and $R^6$ respectively;

with silver cyanate, in a suitable aprotic solvent, for instance dichloromethane, followed by treating with an alcohol compound of formula (a):

$R^{1A}OH$ (III)

in which $R^{1A}$ is $R^1$ as defined for formulae (IA) and (IB) or a group convertible to $R^1$;

in the presence of pyridine, in a carbamate forming reaction, and thereafter, and if so needed;

converting P to hydrogen, and, if necessary, converting an $R^{2A}$, $R^{3A}$, $R^{4A}$, $R^{5A}$ and $R^{6A}$ group to an $R^2$, $R^3$, $R^4$, $R^5$ and $R^6$ group; or (b) chloroformate epi-mutilin compound of formula (IIC):

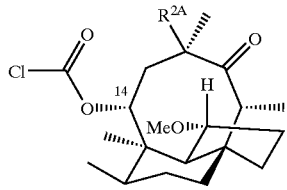

wherein $R^{2A}$ is as hereinbefore defined;

with silver cyanate and then a compound of formula (III), as hereinbefore defined; under carbamate forming conditions as hereinbefore described;

and then treating the product with an acid;

and where required or desired converting an $R^{1A}$ group to an $R^1$ group and an $R^{2A}$ group to an $R^2$ group; or (c) a process corresponding to (a) or (b) in which the chloroformate component comprises $R^{1A}$ and the alcohol component comprises the mutilin nucleus.

12. A pharmaceutical composition comprising a compound or salt according to claim 1 and a pharmaceutically acceptable carrier.

13. A method of treating microbial infections which comprises administering a compound or salt according to claim 1 to a patient in need thereof.

* * * * *